United States Patent [19]

Gillard et al.

[11] Patent Number: 4,940,719

[45] Date of Patent: * Jul. 10, 1990

[54] TETRAHYDROCARBAZOLE ESTERS, PHARMACEUTICAL COMPOSITIONS AND USE

[75] Inventors: John W. Gillard, Baie d'Urfe; Christiane Yoakim; Yvan Guindon, both of Montreal; Yves Girard, Bizard, all of Canada

[73] Assignee: Merck Frosst Canada, Inc., Kirkland, Canada

[ * ] Notice: The portion of the term of this patent subsequent to Feb. 28, 2006 has been disclaimed.

[21] Appl. No.: 101,611

[22] Filed: Sep. 28, 1987

Related U.S. Application Data

[63] Continuation-in-part of Ser. No. 1,711, Jan. 9, 1987, abandoned, which is a continuation-in-part of Ser. No. 845,207, Mar. 27, 1986, abandoned.

[51] Int. Cl.$^5$ .................... A61K 31/395; A61K 31/41; C07D 209/82; C07D 403/02
[52] U.S. Cl. .................................. 514/381; 514/411; 548/253; 548/439
[58] Field of Search .................... 548/444, 439, 253; 514/411, 381

[56] References Cited

U.S. PATENT DOCUMENTS

| | | | |
|---|---|---|---|
| 3,896,145 | 7/1975 | Berger et al. | 548/444 |
| 4,009,181 | 2/1977 | Berger et al. | 548/439 |
| 4,057,559 | 11/1977 | Asselin et al. | 548/439 |
| 4,808,608 | 2/1989 | Guindon et al. | 514/411 |

OTHER PUBLICATIONS

Shen et al, The Development of Antiasthmatic Drugs III, Butterworth Publisher, Kent, Engl 1981 pp. 315–317 and 331–335.

Primary Examiner—Robert W. Ramsuer
Attorney, Agent, or Firm—Gabriel Lopez; Hesna J. Pfeiffer; Charles M. Caruso

[57] ABSTRACT

Tetrahydrocarbazole esters are disclosed. The compounds act as prostaglandin and thromboxane antagonists and are useful in treating asthma, diarrhea, hypertension, angina, platelet aggregation, cerebral spasm, premature labor, spontaneous abortion and dysmenorrhea and nephrotoxicity caused by cyclosporin A and as cytoprotective agents.

14 Claims, No Drawings

TETRAHYDROCARBAZOLE ESTERS, PHARMACEUTICAL COMPOSITIONS AND USE

CROSS-REFERENCE TO RELATED APPLICATIONS

This application is a continuation-in-part of U.S. Ser. No. 001,711, filed Jan. 9, 1987, now abandoned which in turn is a continuation-in-part of U.S. Ser. No. 845,207, filed Mar. 27, 1986 now abandoned.

BACKGROUND OF THE INVENTION

This invention relates to prostaglandin antagonists useful in treating a variety of conditions, such as allergic asthma where excessive contractile activity of prostaglandins and prostaglandin biosynthetic intermediates occur.

These compounds antagonize the actions of contractile prostaglandins, such as $PGF_{2\alpha}$, $PGG_2$, $PGH_2$, $PGD_2$ and $TXA_2$. The use of agents which act as prostaglandin antagonists offers new approaches to therapy in a number of disease states. For example, certain prostaglandins, such as $PGF_{2\alpha}$, $PGD_2$, $PGG_2$, and $PGH_2$, are potent bronchospastic agents. Indeed human asthmatics have been shown to be especially sensitive to the bronchial constricting action of $PGF_{2\alpha}$.

The compounds of the present invention are also antithrombotic agents. Thus, they are useful in the treatment and/or prevention of thromboembolic diseases such as arterial thrombosis and those involving platelet deposition, e.g. prothesis.

In addition to the involvement of contractile prostaglandins in asthma, prostaglandins are known to play a role in other allergic conditions, as well as, diarrhea, hypertension, angina, platelet aggregation, cerebral spasm, cerebral ischemia, arrythmia, circulatory shock, sudden death, atherosclerosis, myocardial ischemia, premature labor, spontaneous abortion, dysmenorrhea, glomerular nephritis, and systemic lupus erythematosis. Consequently, the compounds of this invention will alleviate the above mentioned diseases.

The compounds of the present invention are also useful as agents for protection against the nephrotoxicity caused by cyclosporin A and related drugs.

In addition to the prostaglandin antagonist actions, the compounds of this invention are inhibitors of the biosynthesis of 5-lipoxygenase metabolites of arachidonic acid, such as 5-HPETE, 5-HETE and the leukotrienes. Leukotrienes $B_4$, $C_4$, $D_4$ and $E_4$ are known to contribute to various disease conditions such as asthma, psoriasis, pain, ulcers and systemic anaphylaxis. Thus inhibition of the synthesis of such compounds will alleviate these and other leukotriene-related disease states.

The compounds of the present invention may be used to treat or prevent mammalian (especially, human) disease states such as erosive gastritis; erosive esophagitis; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

Certain 9-benzyl-1,2,3,4-tetrahydrocarbazole acetic acids or esters thereof are shown as chemical intermediates in the preparation of carbazoles that are known in the art as anti-inflammatory, analgesic and anti-rheumatic agents (see U.S. Pat. No. 3,896,145 and British Patent 1,385,620). Certain 9-benzyl-1,2,3,4-tetrahydrocarbazole carboxylic acids are known in the art as anti-inflammatory, analgesic and anti-rheumatic agents (see U.S. Pat. Nos. 3,868,387; 4,009,181; 3,905,998 and 3,758,496), and 9-benzylcarbazole carboxylic acids (U.S. Pat. Nos. 3,956,295 and 4,057,640) and 9-benzylcarbazole acetic acids and esters thereof (U.S. Pat. No. 3,896,145 and British Patent 1,385,620) are known as anti-inflammatory, analgesic and anti-rheumatic agents. None of these compounds, however, are shown to be prostaglandin or thromboxane antagonists or inhibitors of leukotriene biosynthesis.

DESCRIPTION OF THE INVENTION

One embodiment of the present invention is a pharmaceutical composition containing a compound of Formula I:

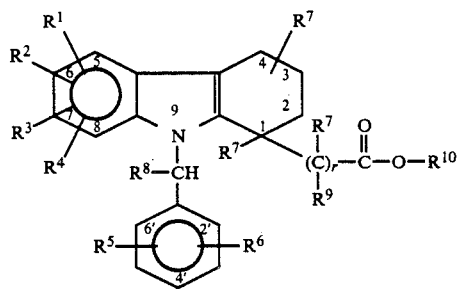

wherein:
$R^1$, $R^2$, $R^3$, $R^4$, $R^5$ and $R^6$ are each independently selected from:
(1) hydrogen;
(2) alkyl having 1 to 6 carbons;
(3) alkenyl having 2 to 6 carbons;
(4) $-(CH_2)_nM$ wherein n is 0 to 3 and M is
 (a) $OR^{11}$;
 (b) halogen;
 (c) $CF_3$;
 (d) $SR^{11}$;
 (e) phenyl or substituted phenyl;
 (f) $COOR^{12}$;

(g) 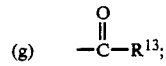

(h) tetrazole;

(i) 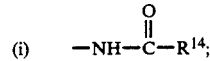

(j) $-NR^{12}R^{12}$;
(k) $-NHSO_2R^{15}$;

(l) 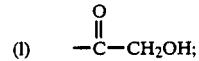

(m) $-SOR^{11}$;
(n) $-CONR^{12}R^{12}$;
(o) $-SO_2NR^{12}R^{12}$;
(p) $-SO_2R^{11}$;
(q) $NO_2$;

(r) $-O-\overset{O}{\underset{\|}{C}}-R^{13}$;

(s) $-O-\overset{O}{\underset{\|}{C}}-NR^{12}R^{12}$;

(t) $-O-\overset{O}{\underset{\|}{C}}-OR^{14}$;

(u) CN;
(v) $N_3$;

$R^7$ is H or alkyl of 1 to 6 carbons;
$R^8$ is H or alkyl of 1 to 6 carbons;
each $R^9$ is independently H, OH, $C_1$ to $C_4$-O-alkyl or alkyl of 1 to 4 carbons;
$R^{10}$ is lower alkyl, substituted or unsubstituted 2-phenethyl, substituted or unsubstituted benzyl, substituted or unsubstituted phenyl, or $$-(CH_2)_r-C(R^7)_2-(CH_2)_r-R^{16}$$

each $R^{11}$ is independently H; $C_1$ to $C_6$ alkyl; benzyl; phenyl or substituted phenyl;
each $R^{12}$ is independently H, phenyl, benzyl or $C_1$ to $C_6$ alkyl;
each $R^{13}$ is independently H, $(CH_2)_mCOOR^{12}$ wherein m is 0 to 4, $C_1$ to $C_6$ alkyl, $CF_3$, phenyl, or substituted phenyl;
each $R^{14}$ is independently $C_1$ to $C_6$ alkyl, benzyl or phenyl;
each $R^{15}$ is independently $C_1$ to $C_6$ alkyl, 4-methylphenyl, phenyl, or $CF_3$;
$R^{16}$ is (A) a monocyclic or bicyclic heterocyclic radical containing from 3 to 12 nuclear carbon atoms and 1 or 2 nuclear heteroatoms selected from N, S, or O and with each ring in the heterocyclic radical being formed of 5 or 6 atoms, or (B) the radical $W-R^{17}$;
$R^{17}$ contains up to 21 carbon atoms and is (1) a hydrocarbon radical or (2) an acyl radical of an organic acyclic or monocyclic carboxylic acid containing not more than 1 heteroatom in the ring;
W is O, S or NH;
r is 1 to 6
t is 0 to 3
or a pharmaceutically acceptable salt thereof.

Preferred compositions of the present invention contain a compound of formula I wherein:
$R^1$, $R^2$, $R^3$, $R^4$, $R^5$ and $R^6$ are each independently selected from:
(1) hydrogen;
(2) alkyl having 1 to 6 carbons;
(3) alkenyl having 2 to 6 carbons;
(4) $-(CH_2)_nM$ wherein n is 0 or 1 and M is as defined previously for Formula I;
and the remaining substituents are as defined previously for Formula I.

More preferred compositions of the present invention contain a compound of Formula I. wherein:
$R^1$, $R^2$, $R^3$, $R^4$, $R^5$ and $R^6$ are each independently selected from:
(1) hydrogen;
(2) alkyl having 1 to 6 carbons;
(3) alkenyl having 2 to 6 carbons;
(4) M, wherein M is as defined initially for Formula I;
r is 1 or 2; and the remaining substituents are as defined initially for Formula I.

Most preferred compositions of the present invention contain a compound of Formula I. wherein:
$R^1$, $R^2$, $R^3$, $R^4$, $R^5$ and $R^6$ are each independently selected from:
(1) hydrogen;
(2) alkyl having 1 to 6 carbons;
(3) M wherein M is
  (a) $OR^{11}$;
  (b) halogen;
  (c) $CF_3$;
  (d) $SR^{11}$;
  (e) $COOR^{12}$;

(f) $-\overset{O}{\underset{\|}{C}}-R^{13}$;

(g) tetrazole;
  (h) $-SOR^{11}$;
  (i) $-CONR^{12}R^{12}$;
  (j) $-SO_2NR^{12}R^{12}$;
  (k) $-SO_2R^{11}$;

(l) $-O-\overset{O}{\underset{\|}{C}}-R^{13}$;

(m) CN;
  (n) $N_3$;
each $R^9$ is independently H, or alkyl of 1 to 4 carbons;
$R^{10}$ is lower alkyl, $-C(R^7)_2-O-C(O)-R^7$ or

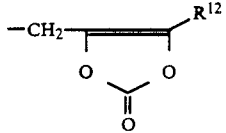

r is 1 and the remaining substituents are as defined initially for Formula I.

In the above most preferred embodiment, those compounds are particularly preferred wherein:
$R^1$ and $R^2$ are hydrogen;
$R^3$ is selected from hydrogen, alkyl having 1 to 6 carbons, halogen, $CF_3$, or CN;
$R^4$ is selected from halogen or $CF_3$;
$R^5$ is selected from hydrogen, halogen or $CF_3$;
$R^6$ is selected from halogen, $-COR^{15}$, $-SO_2NR^{12}R^{12}$, or $-SO_2R^{14}$;
and the remaining substituents are as defined in the most preferred embodiment.

Another embodiment of the present invention relates to novel compounds of Formula I:

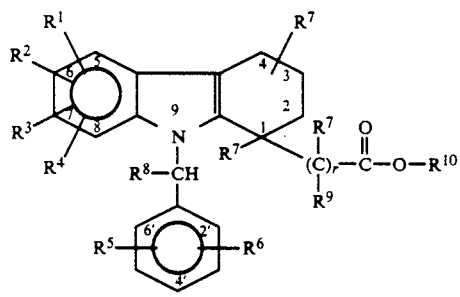

wherein:

$R^1$, $R^2$, $R^3$, $R^4$, $R^5$ and $R^6$ are each independently selected from:
(1) hydrogen;
(2) alkyl having 1 to 6 carbons;
(3) alkenyl having 2 to 6 carbons;
(4) —$(CH_2)_nM$ wherein n is 0 to 3 and M is
 (a) $OR^{11}$;
 (b) halogen;
 (c) $CF_3$;
 (d) $SR^{11}$;
 (e) phenyl or substituted phenyl;
 (f) $COOR^{12}$;

(g) 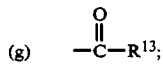

(h) tetrazole;

(i) 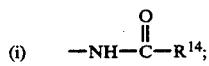

(j) —$NR^{12}R^{12}$;
(k) —$NHSO_2R^{15}$;

(l) 

(m) —$SOR^{11}$;
(n) —$CONR^{12}R^{12}$;
(o) —$SO_2NR^{12}R^{12}$;
(p) —$SO_2R^{11}$;
(q) $NO_2$;

(r) 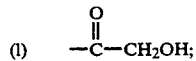

(s) 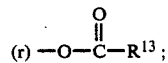

(t) 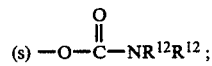

(u) CN;
(v) $N_3$;
provided that when $R^1$, $R^2$, $R^3$ or $R^4$ is alkyl having 1 to 6 carbons, it is not located at position 6;
$R^7$ is H or alkyl of 1 to 6 carbons;
$R^8$ is H or alkyl of 1 to 6 carbons;
each $R^9$ is independently H, OH, $C_1$ to $C_4$-O-alkyl or alkyl of 1 to 4 carbons;
$R^{10}$ is lower alkyl, substituted or unsubstituted 2-phenethyl, substituted or unsubstituted benzyl, substituted or unsubstituted phenyl, or

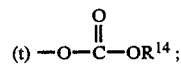

each $R^{11}$ independently is H; $C_1$ to $C_6$ alkyl; benzyl; phenyl or substituted phenyl;
each $R^{12}$ is independently H, phenyl, benzyl or $C_1$ to $C_6$ alkyl; and,
each $R^{13}$ is independently H, $(CH_2)_mCOOR^{12}$ wherein m is 0 to 4, $C_1$ to $C_6$ alkyl, $CF_3$, phenyl, or substituted phenyl;
each $R^{14}$ is $C_1$ to $C_6$ alkyl, benzyl or phenyl;

each $R^{15}$ is $C_1$ to $C_6$ alkyl, 4-methylphenyl, phenyl, or $CF_3$;
$R^{16}$ is (A) a monocyclic or bicyclic heterocyclic radical containing from 3 to 12 nuclear carbon atoms and 1 or 2 nuclear heteroatoms selected from N, S, or O and with each ring in the heterocyclic radical being formed of 5 or 6 atoms, or (B) the radical W-$R^{17}$;
$R^{17}$ contains up to 21 carbon atoms and is (1) a hydrocarbon radical or (2) an acyl radical of an organic acyclic or monocyclic carboxylic acid containing not more than 1 heteroatom in the ring;
W is O, S or NH;
r is 1 to 6
t is 0 to 3
or a pharmaceutically acceptable salt thereof.

As used herein, the terms "each independently" or the equivalents thereof are employed to describe a number of possible position isomers and/or structural variations. For example, as described above, the following unit is attached to position 1 of the tetrahydrocarbazole ring:

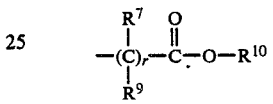

The letter r represents possible alkane chains of from 1 to 6 carbon atoms, each having the $R^7$ and $R^9$ substituent groups. On each carbon atom of the alkane chain, the $R^7$ and/or $R^9$ substituent may be different. The above description therefore contemplates structures such as the following for the segment —$(CR^7R^9)_r$—:

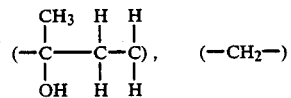

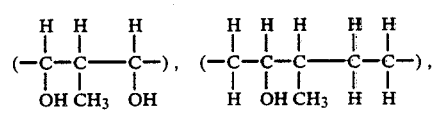

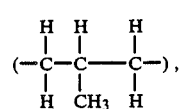

and the like.

Substituted phenyl, substituted benzyl, and substituted phenethyl signifies the presence of 1 or 2 substituents on the benzene ring selected from $C_1$ to $C_3$ alkyl, halogen, CN, $CF_3$, $COOR^{12}$, $CH_2COOR^{12}$, or $C_1$ to $C_3$ alkoxy.

The alkyl groups referred to above may be straight chain or branched or may include cycloalkyl groups. As used herein, the term "lower" as applied to alkyl, acyl, alkoxy and the like, unless stated otherwise refers to groups having 1 to 6 carbon atoms. Halogen or halo means fluoro, chloro, bromo and/or iodo.

The esters when $R^{10}$ is —$(CH_2)_r$—$C(R^7)_2$—$(CH_2)_r$—$R^{16}$ are intended to include the esters such as are described by Saari, et al, J. Med. Chem., 21, 746–753 (1978) and Sakamoto, et al, Chem. Pharm. Bull., 32, 2241–2248 (1984) which are hereby incorporated by reference.

Pharmaceutically acceptable salts of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, tri-methylamine, diethanolamine, diethylamine, triethylamine, tripropylamine, ethanolamine, 2-dimethylaminoethanol, 2diethylaminoethanol, tomethamine, lysine, arginine, histidine, caffeine, procaine, hydrabamine, choline, imidazole, betaine, ethylenediamine, glucosamine, methylglucamine, theobromine, purines piperazine, N,N-dibenzylethylenediamine, piperidine, N-ethyl-piperidine, morpholine, N-ethylmorpholine, polyamine resins and the like.

Preferred novel compounds of the present invention comprise the compound of Formula I wherein:

$R^1$, $R^2$, $R^3$, $R^4$, $R^5$ and $R^6$ are each independently selected from:
(1) hydrogen;
(2) alkyl having 1 to 6 carbons;
(3) alkenyl having 2 to 6 carbons;
(4) —(CH$_2$)$_n$M wherein n is 0 or 1 and M is as defined previously for the compounds of Formula I;
and the remaining substituents are as defined previously for the compounds of Formula I.

More preferred novel compounds of the present invention comprise a compound of Formula I wherein:
$R^1$, $R^2$, $R^3$, $R^4$, $R^5$ and $R^6$ are each independently selected from:
(1) hydrogen;
(2) alkyl having 1 to 6 carbons;
(3) alkenyl having 2 to 6 carbons;
(4) M, wherein M is as defined initially for the compounds of Formula I;
r is 1 or 2; and the remaining substituents are as defined initially for the compounds of Formula I.

Most preferred novel compounds of the present invention comprise the compound of Formula I wherein:
$R^1$, $R^2$, $R^3$, $R^4$, and $R^5$ are each independently selected from:
(1) hydrogen;
(2) alkyl having 1 to 6 carbons;
(3) M wherein M is
 (a) OR$^{11}$;
 (b) halogen;
 (c) CF$_3$;
 (d) SR$^{11}$;
 (e) COOR$^{12}$;

(f) 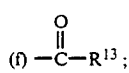;

(g) tetrazole;
(h) —SOR$^{11}$;
(i) —CONR$^{12}$R$^{12}$;
(j) —SO$_2$NR$^{12}$R$^{12}$;
(k) —SO$_2$R$^{11}$;

(l) 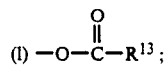;

(m) CN;
(n) N$_3$;

$R^6$ is located at position 3' or 4' and is selected from:
(1) alkyl having 1 to 6 carbons;
(2) M wherein M is
 (a) OR$^{11}$;
 (b) halogen;
 (c) CF$_3$;
 (d) SR$^{11}$;
 (e) COOR$^{12}$;

(f) 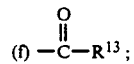;

(g) tetrazole;
(h) —SOR$^{11}$;
(i) —CONR$^{12}$R$^{12}$;
(j) —SO$_2$NR$^{12}$R$^{12}$;
(k) —SO$_2$R$^{11}$;

(l) 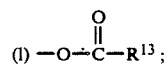;

(m) CN;
(n) N$_3$;

provided that when $R^1$, $R^2$, $R^3$ or $R^4$ is alkyl having 1 to 6 carbons, it is not located at position 6.

each $R^9$ is independently H, or alkyl of 1 to 4 carbons;
$R^{10}$ is lower alkyl,

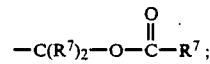

or 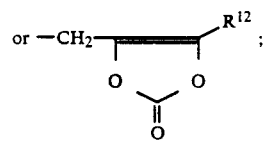

r is 1 and the remaining substituents are as defined initially for the compounds of Formula I.

In the above most preferred embodiment, those compounds are particularly preferred wherein:
$R^1$ and $R^2$ are hydrogen;
$R^3$ is selected from hydrogen, alkyl having 1 to 6 carbons, halogen, CF$_3$, or CN;
$R^4$ is selected from halogen or CF$_3$;
$R^5$ is selected from hydrogen, halogen or CF$_3$;
$R^6$ is selected from halogen, —COR$^{15}$, —SO$_2$NR$^{12}$R$^{12}$, or —SO$_2$R$^{14}$;
and the remaining substituents are as defined in the most preferred embodiment.

TABLE 1
Novel Tetrahydrocarbazole Alkanoic Esters

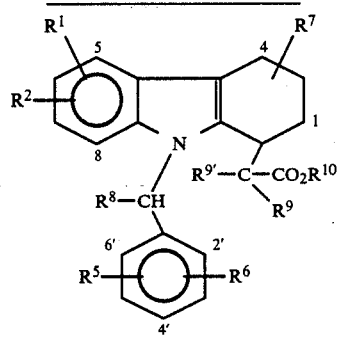

| Compound | R¹ | R² | R⁵ | R⁶ | R⁹, R⁹' | R⁷ | R⁸ | R¹⁰ |
|---|---|---|---|---|---|---|---|---|
| 1 (Ex. 1) | 6-F | H | 4'-Cl | H | H, H | H | H | Et |
| 2 (Ex. 4) | 6-OMe | H | 4'-Cl | H | H, H | H | H | Et |
| 3 (Ex. 18) | 6-F (−) isomer | H | 4'-Cl | H | H, H | H | H | Me |
| 4 (Ex. 19) | 6-F (+) isomer | H | 4'-Cl | H | H, H | H | H | Me |
| 5 (Ex. 5) | 6-F | H | H | H | H, H | H | H | Et |
| 6 (Ex. 6) | 6-F | H | 4'-OMe | H | H, H | H | H | Et |
| 7 (Ex. 7) | 6-F | H | 3'-Cl | 4'-Cl | H, H | H | H | Et |
| 8 (Ex. 8) | 6-F | H | H | H | H, H | H | Me | Et |
| 9 (Ex. 9) | H | H | 4'-Cl | H | H, H | H | H | Et |
| 10 (Ex. 10) | 6-Cl | H | 4'-Cl | H | H, H | H | H | Et |
| 11 (Ex. 11) | 8-Me | H | 4'-Cl | H | H, H | H | H | Et |
| 12 (Ex. 12) | 6-Br | H | 4'-Cl | H | H, H | H | H | Et |
| 13 (Ex. 13) | 6-Me | H | 4'-Cl | H | H, H | H | H | Et |
| 14 (Ex. 15) | 8-F | H | 4'-Cl | H | H, H | H | H | Et |
| 15 | 6-F | H | 4'-Cl | H | H, H | 3-t-Bu | H | CH₂C₆H₅ |
| 16 | 5-F | H | 4'-Cl | H | H, H | H | H | CH₂OAc |
| 17 | 7-F | H | 4'-Cl | H | H, H | H | H | CH₂-(4-methyl-1,3-dioxol-2-one-5-yl) |
| 18 (Ex. 16) | 5-Cl | 7-Cl | 4'-Cl | H | H, H | H | H | Et |
| 19 (Ex. 17) | 6-Cl | 8-Cl | 4'-Cl | H | H, H | H | H | Et |
| 20 | 6-F | H | 4'-Cl | H | Me, H | H | H | CH₂-(3-methyl-2,5-dioxoimidazolidin-1-yl) |
| 21 | 6-F | H | 4'-Cl | H | Me, Me | H | H | CH₂-(2-oxopyrrolidin-1-yl) |
| 22 | 6-F | H | 4'-Cl | H | H, H | 1-Me | H | CH₂-(2,5-dioxopyrrolidin-1-yl) |
| 23 (ex 20) | 6-CH(Me)₂ | H | 4'-Cl | H | H, H | H | H | Et |
| 24 (ex 21) | 6-C(Me)₃ | H | 4'-Cl | H | H, H | H | H | Et |
| 25 (ex 22) | 6-CF₃ | H | 4'-Cl | H | H, H | H | H | Et |
| 26 (ex 23) | 6-SMe | H | 4'-Cl | H | H, H | H | H | Et |
| 27 (ex 24) | 6-SOMe | H | 4'-Cl | H | H, H | H | H | Et |
| 28 (ex 25) | 6-SO₂Me | H | 4'-Cl | H | H, H | H | H | Et |
| 29 (ex 26) | 8-CH(Me)₂ | H | 4'-Cl | H | H, H | H | H | Et |
| 30 (ex 27) | 8-SMe | H | 4'-Cl | H | H, H | H | H | Me |

TABLE 1-continued

Novel Tetrahydrocarbazole Alkanoic Esters

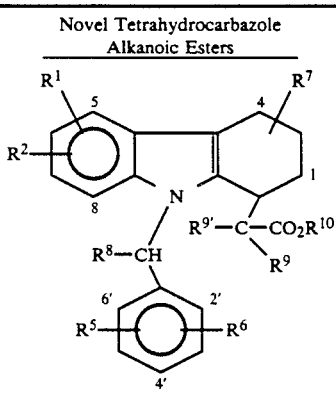

| Compound | $R^1$ | $R^2$ | $R^5$ | $R^6$ | $R^9, R^{9'}$ | $R^7$ | $R^8$ | $R^{10}$ |
|---|---|---|---|---|---|---|---|---|
| 31 (ex 28) | 8-SOMe | H | 4'-Cl | H | H, H | H | H | Me |
| 32 (ex 29) | 6-F | H | 4'-Cl | H | H, H | 3-Me | H | Et |
| 33 (ex 30) | 6-F | 8-F | 4'-Cl | H | H, H | H | H | Me |
| 34 (ex 31) | 6-Me | 8-Me | 4'-Cl | H | H, H | H | H | Me |
| 35 (ex 32) | 6-OMe | 8-Me | 4'-Cl | H | H, H | H | H | Me |
| 36 (ex 33) | 6-F(−)Isomer | 8-F | 4'-Cl | H | H, H | H | H | Me |
| 37 (ex 34) | 6-F(+)Isomer | 8-F | 4'-Cl | H | H, H | H | H | Me |
| 38 (ex 35) | 8-Me(−)Isomer | H | 4'-Cl | H | H, H | H | H | Me |
| 39 (ex 36) | 8-Me(+)Isomer | H | 4'-Cl | H | H, H | H | H | Me |
| 40 (ex 37) | 8-F(−)Isomer | H | 4'-Cl | H | H, H | H | H | Me |
| 41 (ex 38) | 8-F(+)Isomer | H | 4'-Cl | H | H, H | H | H | Me |
| 42 | 6-F | 8-F | 3'-Cl | 4'-Cl | H, H | H | H | Me |
| 43 (ex 40) | 6-F | 8-F | 2'-Cl | 4'-Cl | H, H | H | H | Me |
| 44 | 6-F | 8-F | 4'-OMe | H | H, H | H | H | Me |
| 45 | 6-F | 8-F | 4'-OH | H | H, H | H | H | Me |
| 46 (ex 41) | 6-F | 8-F | 4'-SMe | H | H, H | H | H | Me |
| 47 | 6-F | H | 4'-S(O)Me | H | H, H | H | H | Me |
| 48 (ex 53) | 6-F | 8-F | 4'-NHCOMe | H | H, H | H | H | Me |
| 49 | 6-F | H | 4'-S(O)$_2$Me | H | H, H | H | H | Me |
| 50 | 6-F | H | 4'-F | H | H, H | H | H | Me |
| 51 | 6-F | H | 4'-Br | H | H, H | H | H | Me |
| 52 | 6-F | 8-Me | 4'-Cl | H | H, H | H | H | Me |
| 53 | 6-F | H | 4'-CO$_2$H | H | H, H | H | H | Me |
| 54 | 6-F | H | 4'-CO$_2$Me | H | H, H | H | H | Me |
| 55 | 6-F | 8-F | 4'-n-C$_3$H$_7$ | H | H, H | H | H | Me |
| 56 | 6-F | 8-F | 3'-I | 4'-OH | H, H | H | H | Me |
| 57 | 6-F | 8-F | 4'-I | H | H, H | H | H | Me |
| 58 | 6-N$_3$ | H | 4'-Cl | H | H, H | H | H | Me |
| 59 | 6-F | H | 4'-N$_3$ | H | H, H | H | H | Me |
| 60 (ex. 42) | 6-F | 8-F | 4'-S(O)Me | H | H, H | H | H | Me |
| 61 (ex. 43) | 6-F | 8-F | 4'-S(O)$_2$Me | H | H, H | H | H | Me |
| 62 (ex. 44) | 6-F (−) isomer | 8-F | 4'-S(O)$_2$Me | H | H, H | H | H | Me |
| 63 (ex. 45) | 6-F (+) isomer | 8-F | 4'-S(O)$_2$Me | H | H, H | H | H | Me |
| 64 (ex. 39) | 6-F | 8-F | 2'-Cl | H | H, H | H | H | Me |
| 65 (ex. 46) | 6-F | 8-F | 4'-CF$_3$ | H | H, H | H | H | Me |
| 66 (ex. 47) | 6-F | 8-F | 4'-F | H | H, H | H | H | Me |
| 67 (ex. 48) | 6-F | 8-F | 3'-Cl | H | H, H | H | H | Me |
| 68 (ex. 49) | 6-F | 8-F | 4'-CO$_2$Me | H | H, H | H | H | Me |
| 69 (ex. 50) | 6-F | 8-F | 4'-CONMe$_2$ | H | H, H | H | H | Me |
| 70 (ex. 51) | 6-F | 8-F | 4'-COMe | H | H, H | H | H | Me |
| 71 (ex. 52) | 6-F | 8-F | 4'-SO$_2$NMe$_2$ | H | H, H | H | H | Me |
| 72 (ex. 54) | 6-F | 8-F | 4'-NHSO$_2$Me | H | H, H | H | H | Me |
| 73 (ex. 55) | 6-F | 8-f | 4'-NHCONHMe | H | H, H | H | H | Me |
| 74 (ex. 56) | 6-F | 8-F | 4'-OMe | H | H, H | H | H | Me |
| 75 (ex. 53) (Step III) | 6-F | 8-F | 4'-NH$_2$ | H | H, H | H | H | Me |
| 76 | 6-F | 8-F | 4'-OH | H | H, H | H | H | Me |
| 77 (ex. 53) (Step II) | 6-F | 8F | 4'-NO$_2$ | H | H, H | H | H | Me |

The following reaction schemes illustrate the preparation of the compounds of the present invention:

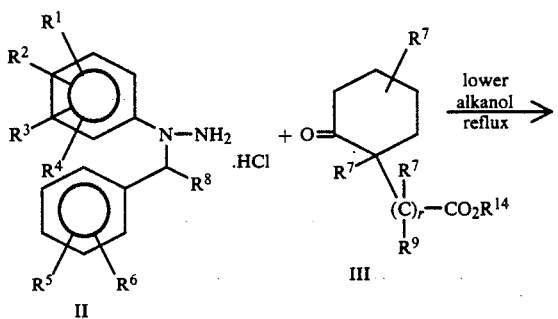

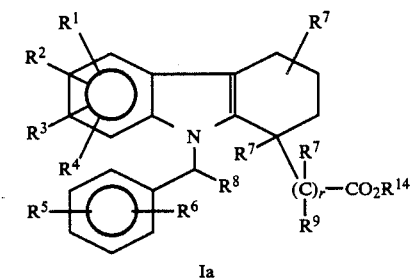

The reaction can be conveniently carried out in an alcohol solvent such as t-butanol, i-butanol, and the like.

The following ketones (1,2,4) of structure III are known in the art, and ketone 3 is readily prepared by procedures analogous to those for the known ketones.

TABLE 2
Ketones of Formula III

| No. | Structure | Reference |
|---|---|---|
| 1. | 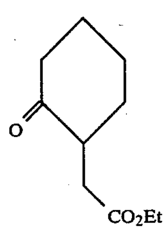 | Ethyl 2-cyclohexanone acetate; commercially available (Aldrich) |
| 2. | 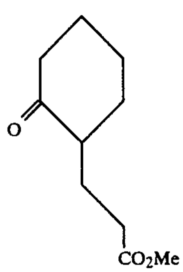 | Methyl 2-cyclohexanone propionate; J.A.C.S. 85 207 (1963) G. Stork, A. Brizzolara, H. Landesman, J. Scmuszkovicz and R. Terrell |
| 3. | 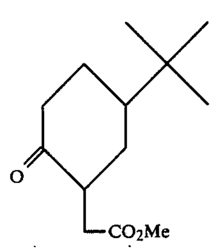 | Methyl 4-t-butyl-2-cyclohexanone acetate |

TABLE 2-continued
Ketones of Formula III

| No. | Structure | Reference |
|---|---|---|
| 4. | 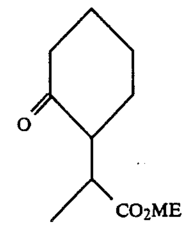 | Methyl 2-(2-cyclohexanone) propionate J.A.C.S. 85 207 (1963) G. Stork, A. Brizzolara, H. Landesman, J. Scmuszkovicz and R. Terrell |
| 5. | 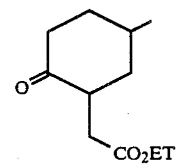 | Ethyl 4-methyl-2-cyclohexanone acetate |

The sequence described above is an application of the Fischer Indole Synthesis. Numerous indole syntheses are described in reviews, such as, for example "Heterocyclic Compounds" Volume 25, Parts I, II, III, W. J. Houlihan (Ed.), Interscience, J. Wiley & Sons, N.Y., 1979. Appropriate manipulations of functional groups using sequences described in such reviews will lead to the compounds of the present invention.

Scheme II
Preparation of Hydrazine Derivatives (II)

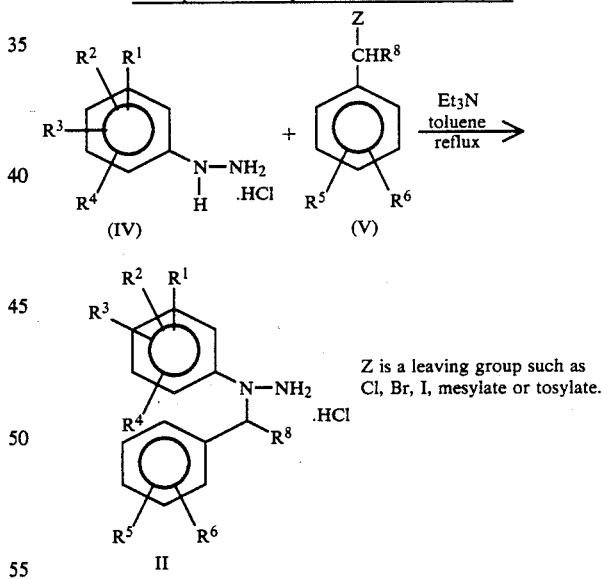

Z is a leaving group such as Cl, Br, I, mesylate or tosylate.

With regard to Scheme II, the preparation of hydrazine starting materials is illustrated by the preparation of 1-(4-chlorobenzyl)-1-(4-methoxyphenyl)hydrazine. A mixture of 10 g of p-methoxyphenylhydrazine hydrochloride, 75 ml of toluene and 11.5 ml of triethylamine was heated at reflux for 60 minutes. Then, 7.1 g of p-chlorobenzyl chloride was added. After stirring 16 hours at reflux, triethylamine hydrochloride was filtered off and washed with ethyl ether. The filtrate and washing were concentrated in vacuo and chromatographed on a silica gel column (hexane-ethyl acetate, 9:1) to give 6.64 g of 1-(4-chlorobenzyl)-1-(4-methoxyphenyl)hydrazine. Other hydrazines, similarly prepared, are also shown in Table 3, below. In Table 3a are shown representative benzylhalides V.

TABLE 3

Hydrazines

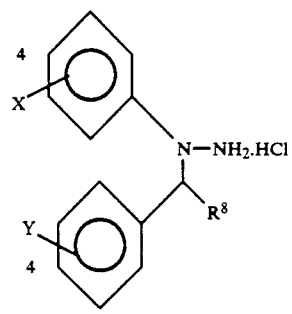

| Compound No. | X | Y | R⁸ | Compound Name |
|---|---|---|---|---|
| 1. | 4-F | 4-Cl | H | 1-(4-chlorobenzyl)-1-(4-fluorophenyl) hydrazine hydrochloride |
| 2. | 3,5-Cl$_2$ | 4-Cl | H | 1-(4-chlorobenzyl)-1-(3,5-dichlorophenyl)hydrazine hydrochloride |
| 3. | 4-OMe | 4-Cl | H | 1-(4-chlorobenzyl)-1-(4-methoxyphenyl) hydrazine hydrochloride |
| 4. | 2-Me | 4-Cl | H | 1-(4-chlorobenzyl)-1-(2-methylphenyl) hydrazine hydrochloride |
| 5. | 4-Me | 4-Cl | H | 1-(4-chlorobenzyl)-1-(4-methylphenyl) hydrazine hydrochloride |
| 6. | 4-Cl | 4-Cl | H | 1-(4-chlorobenzyl)-1-(4-chlorophenyl) hydrazine hydrochloride |
| 7. | H | 4-Cl | H | 1-(4-chlorobenzyl)-1-(phenyl) hydrazine hydrochloride |
| 8. | 4-Br | 4-Cl | H | 1-(4-chlorobenzyl)-1-(4-bromophenyl) hydrazine hydrochloride |
| 9. | 3-F | 4-Cl | H | 1-(4-chlorobenzyl)-1-(3-fluorophenyl) hydrazine hydrochloride |
| 10. | 2,4-Cl$_2$ | 4-Cl | H | 1-(4-chlorobenzyl)-1-(2,4-dichlorophenyl)hydrazine hydrochloride |
| 11. | 4-F | H | H | 1-(benzyl)-1-(4-fluorophenyl) hydrazine hydrochloride |
| 12. | 4-F | 4-OMe | H | 1-(4-methoxybenzyl)-1-(4-fluorophenyl) hydrazine hydrochloride |
| 13. | 4-F | 3,4-Cl$_2$ | H | 1-(3,4-dichlorobenzyl)-1-(4-fluoro-phenyl) hydrazine hydrochloride. |
| 14. | 4-F | H | CH$_3$ | 1-[-1(phenyl)ethyl]-1-(4-fluorophenyl) hydrazine hydrochloride |
| 15. | 2-F | 4-Cl | H | 1-(4-chlorobenzyl)-1-(2-fluorophenyl) hydrazine hydrochloride. |
| 16. | 4-CH(Me)$_2$ | 4-Cl | H | 1-(4-chlorobenzyl)-1-(4-isopropylphenyl)hydrazine hydrochloride |
| 17. | 4-C(Me)$_3$ | 4-Cl | H | 1-(4-chlorobenzyl)-1-(4-tert-butylphenyl)hydrazine)hydrochloride |
| 18. | 4-CF$_3$ | 4-Cl | H | 1-(4-chlorobenzyl)-1-(4-trifluoromethylphenyl)hydrazine hydrochloride |
| 19. | 4-SMe | 4-Cl | H | 1-(4-chlorobenzyl)-1-(4-methylthiophenyl)hydrazine hydrochloride |
| 20. | 2-CH(Me)$_2$ | 4-Cl | H | 1-(4-chlorobenzyl)-1-(2-isopropylphenyl)hydrazine hydrochloride |

TABLE 3a

Benzyl Halides V

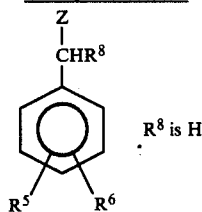

R[8] is H

| Compound No. | Z | R[5] | R[6] | Compound Name |
|---|---|---|---|---|
| 1. | Cl | 4-Cl | H | 4-chlorobenzyl chloride (ALDRICH) |
| 2. | Cl | 4-OMe | H | 4-methoxybenzyl chloride (ALDRICH) |
| 3. | Cl | 2-Cl | 4-Cl | 2,4-dichlorobenzyl chloride (ALDRICH) |
| 4. | Br | 2-Cl | H | 2-chlorobenzyl bromide (ALDRICH) |
| 5. | Br | 3-Cl | H | 3-chlorobenzyl bromide (ALDRICH) |
| 6. | Br | 4-F | H | 4-fluorobenzyl bromide (ALDRICH) |
| 7. | Br | 4-CF$_3$ | H | 4-trifluoromethylbenzyl bromide (ALDRICH) |
| 8. | Cl | 4-CO$_2$Me | H | 4-carbomethoxybenzyl chloride (J.A.C.S. 1950, 72, 5152) |
| 9. | Cl | 4-SMe | H | 4-methylthiobenzyl chloride (C.A.:56:4773 (1962)) |
| 10. | Cl | 4-SOMe | H | 4-methylsulfinylbenzyl chloride (C.A.:84:105277h (1976)) |
| 11. | Cl | 4-SO$_2$Me | H | 4-methylsulfonylbenzyl chloride (C.A:78:1113259 (1973)) |
| 12. | Br | 4-NO$_2$ | H | 4-nitrobenzyl bromide (ALDRICH) |
| 13. | Cl | 4-CONMe$_2$ | H | 4-dimethylcarboxamidobenzyl chloride |
| 14. | Cl | 4-SO$_2$NMe$_2$ | H | 4-dimethylaminosulfonylbenzyl chloride (ALDRICH) |

TABLE 3a-continued

Benzyl Halides V

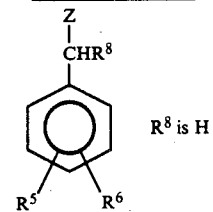

R[8] is H

| Compound No. | Z | R[5] | R[6] | Compound Name |
|---|---|---|---|---|
| 15. | Cl | 4-CO$_2$H | H | (C.A.:84:135484r (1976)) 4-carboxybenzyl chloride (ALDRICH) |
| 16. | Cl | 4-COMe | H | 4-acetylbenzyl chloride (C.A.:93:2399945 (1980)) |

To prepare certain esters representative of the Formula I compounds, it may be advantageous to first prepare the lower alkyl esters as illustrated in Scheme I. Hydrolysis of these lower alkyl esters by conventional means, such as by using NaOH or KOH in aqueous ethanol, followed by acidification, then produces the corresponding carboxylic acids VI, as illustrated in Scheme III. The carboxylic acid is then reacted with an alkylating agent, R[10]—Z, in the presence of a suitable base and solvent combination, such as for example, Na$_2$CO$_3$ in acetone or triethylamine in dimethylformamide, to produce the esters Ib. Compounds 15, 16, 17, 20, 21 and 22 of Table I are conveniently prepared by this method.

Another method of preparing the esters of Formula I from the acid, VI consists of treating the latter with a diazoalkane (such as diazomethane) in a suitable non-reactive solvent such as ether or methanol to obtain an ester Ic. Other methods are shown in Ogliaruso and Wolfe in Patai, *The Chemistry of Acid Derivatives*, Supplement B, Wiley, New York, 1979, (pp. 411–436) which is hereby incorporated by reference.

Scheme III
Preparation of Formula I Compounds

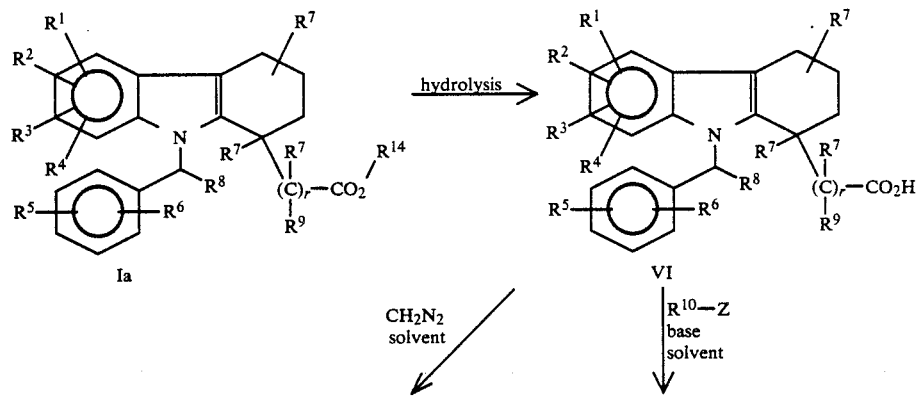

Scheme III
Preparation of Formula I Compounds

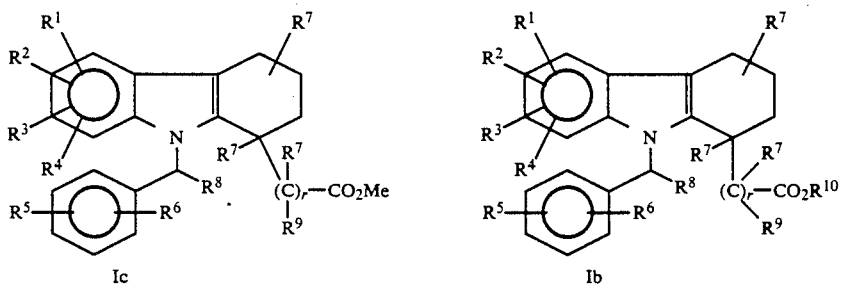

In those instances when asymmetric centers are present, more than one stereoisomer is possible, and all possible isomeric forms are deemed to be included within the planar structural representations shown. Optically active (R) and (S) isomers may be resolved using conventional techniques known to the skilled artisan.

Among the resolved isomers in Table 1, the esters of the minus (−) acids, compounds 3, 36, 38 and 40 are preferred.

Scheme IV
Alternative Preparation of Formula I Compounds

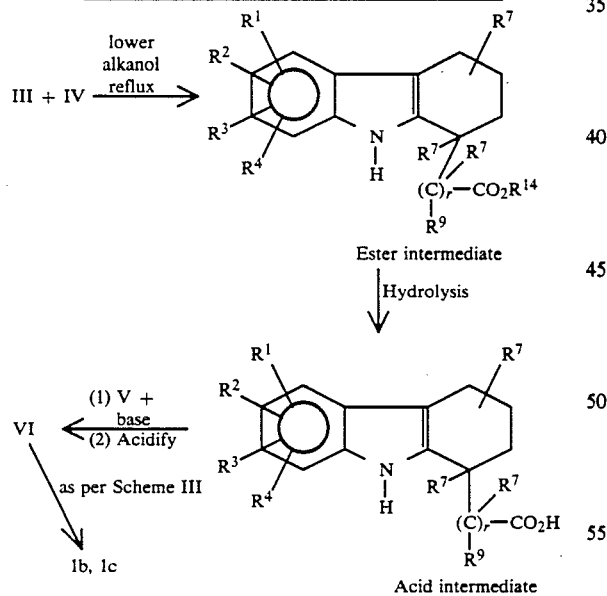

Scheme IV illustrates an alternative synthesis of the compounds of Formula I. In this Scheme a Fischer indole synthesis is carried out using a phenylhydrazine IV and the kétone III, followed by hydrolysis. The acid intermediate is then N-benzylated with the reagent V, preferably using a strong base such as potassium t-butoxide to effect the reaction. Acidification of the reaction mixture then yields the acid VI which can be converted to compounds of Formula I as indicated in Scheme III.

Scheme V
Preparation of Sulfoxides and Sulfones of Formula I compounds

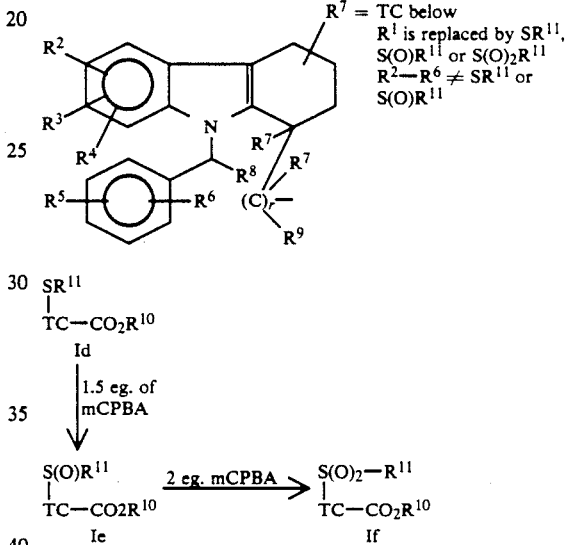

In Scheme V is illustrated a method of preparing derivatives of Formula I in which one of the substituents among $R^1$-$R^4$ is a sulfoxide or a sulfone. It will be obvious to one skilled in the art that a sulfoxide or sulfone derivative of $R^5$ or $R^6$ could be prepared in the same way.

Ester Id (a representative of I) is prepared according to Scheme I or Scheme III. Treatment of Id with a limited amount of an oxidizing agent such as m-chloroperbenzoic acid yields the sulfoxide ester Ie. Further treatment of Ie with the oxidizing agent, or treatment of Id with an excess (>2 eq.) of the oxidizing agent yields the sulfone ester If.

Scheme VI
Preparation of Hydrazine Denivatives IV

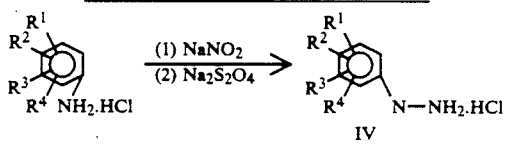

With regard to Scheme VI, the preparation of hydrazine starting materials is illustrated by preparation of 4-methylthiophenyl hydrazine hydrochloride. 4-Methylthioaniline (13.9 g) was added dropwise to cold HCl (6N) (50 mL) and stirred for 5 min in an ice bath.

A solution of NaNO₂ in water (7.25 g, 15 mL) was then added dropwise and stirred for 15 min. The cold diazonium salt was then cannulated into a stirred cold solution of Na₂S₂O₄ in water (50 g, 250 mL). After 20 min, ether (200 mL) was added and the reaction mixture basified with NaOH(10N). The ether layer was decanted, washed with brine, dried over Na₂SO₄ and HCl gas was passed through the ether solution to form the hydrochloride salt which precipitated out. After filtration, there was obtained 7.0 g of pure final product. Other hydrazines, similarly prepared, are also shown in Table 4, below.

TABLE 4
HYDRAZINES IV (structure: benzene ring with substituents $R^1$, $R^2$, $R^3$, $R^4$ and NHNH$_2$·HCl)

| Compound No. | $R^1$ | $R^2$ | Compound Name |
|---|---|---|---|
| 1 | 4-SMe | H | 4-methylthiophenyl hydrazine hydrochloride |
| 2 | 2-CH(Me)₂ | H | 2-isopropylphenyl hydrazine hydrochloride |
| 3 | 2-SMe | H | 2-methylthiophenyl hydrazine hydrochloride |
| 4 | 2-Me | 4-Me | 2,4-dimethylphenyl hydrazine hydrochloride |
| 5 | 2-Me | 4-OMe | 4-methoxy-2-methylphenyl hydrazine hydrochloride |

$R^3 = R^4 = H$

The prostaglandin antagonist properties of the compositions and compounds of the present invention can be demonstrated by the biological assay described below.

Agonist-induced Bronchonconstriction in Anesthetized Guinea Pigs (Konzett-Rossler)

Male Hartley strain guinea-pigs (350–500 g) are anesthetized with urethane (1.5 g/kg i.p.), given succinylcholine chloride (5 mg/kg s.c.) to suppress spontaneous respiration and artificially ventilated at 60 breaths/minute. Changes in insufflation pressure (resistance to inflation) are measured using a Statham PM-5E differential pressure transducer and recorded on a Beckman Type R-Dynograph. Increases in insufflation pressure are induced at 20 minute intervals with bolus intravenous injections of arachidonic acid (0.5 mg/kg), or U-44069 (15(S)-hydroxy-9α, 11α-(epoxymethano)-prosta-5-cis, 13-trans-dienoic acid) (a stable prostaglandin endoperoxide analogue) (2 μg/kg). After obtaining at least two reproducible control responses to the agonist under study, the antagonist activity of the test compound is determined. In order to assess antagonist activity, the test compound (in solution or suspension) or drug vehicle (1 ml/kg) is administered intravenously in cumulative doses 5 minutes prior to each subsequent agonist challenge. Reductions of the agonist response are calculated as a percent of the control response which immediately preceded the initial antagonist or vehicle dose. ED₅₀ values (dose required to inhibit the insufflation pressure increase by 50 percent) are calculated by regression analysis.

In a variation of the assay, the test compound is administered as a single dose intraduodenally (injected into the duodenum which has been previously exposed through a ventral mid-line incision) 10 minutes before challenge with arachidonic acid (0.5 mg/kg) or U-44069 (2 μg/kg). The agonist challenge is continued 10 minutes after administration of the antagonist and every 20 minutes thereafter for a period of up to 2 hours. Reduction of the post drug response is calculated as a percent of the pre-drug control response. This variation of the assay also permits the evaluation of antagonists with a delayed onset of action.

Compounds of Formula I can be tested using the following assay to determine their mammalian leukotriene biosynthesis inhibiting activity.

Rat Peritoneal Polymorphonuclear (PMN) Leukocyte Assay

Rats under ether anesthesia are injected (i.p.) with 8 ml of a suspension of sodium caseinate (6 grams in ca. 50 ml water). After 15–24 hr. the rats are sacrificed (CO₂) and the cells from the peritoneal cavity are recovered by lavage with 20 ml of buffer (Eagles MEM containing 30 mM HEPES adjusted to pH 7.4 with NaOH). The cells are pelleted (350×g, 5 min.), resuspended in buffer with vigorous shaking, filtered, through lens paper, recentrifuged and finally suspended in buffer at a concentration of 10 cells/ml. A 500 μl aliquot of PMN suspension and test compound are preincubated for 2 minutes at 37° C., followed by the addition of 10 μM A-23187. The suspension is stirred for an additional 4 minutes then bioassayed for LTB₄ content by adding an aliquot to a second 500 μl portion of the PMN at 37° C. The LTB₄ produced in the first incubation causes aggregation of the second PMN, which is measured as a change in light transmission. The size of the assay aliquot is chosen to give a submaximal transmission change (usually −70%) for the untreated control. The percentage inhibition of LTB₄ formation is calculated from the ratio of transmission change in the sample to the transmission change in the compound-free control.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cyto-protective compounds will prevent gastric lesions induced by oral administration of strong acids, strong bases, ethanol, hypertonic saline solutions and the like.

Two assays can be used to measure cyto-protective ability. These assays are; (A) an ethanol-induced lesion assay and (B) an indomethacin-induced ulcer assay and are described in EP 140,684.

The magnitude of a prophylactic or therapeutic dose of a compound of Formula I will, of course, vary with the nature or the severity of the condition to be treated and with the particular compound of Formula I and its route of administration. In general, the daily dose range for anti-asthmatic, anti-allergic, or anti-thrombotic use lies within the range of from about 0.01 mg to about 100 mg per kg body weight of a mammal.

The exact amount of a compound of Formula I to be used as cytoprotective agent will depend on, inter alia, whether it is being administered to heal damaged cells or to avoid future damage, on the nature of the damaged cells (e.g., gastro-intestinal ulcerations vs. nephrotic necrosis), and on the nature of the causative agent. An example of use of a compound of Formula I to avoid future damage is coadministration with a non-steroidal anti-inflammatory drug (for example, indomethacin).

The effective daily dosage level for compounds of Formula I inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

Any suitable route of administration may be employed for providing a mammal, especially a human with an effective dosage of a compound of Formula I. For example, oral, rectal, topical, parenteral, ocular, nasal, buccal, intravenous and the like may be employed. Dosage forms include tablets, troches, dispersions, suspensions, solutions, capsules, creams, ointments, aerosols and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, or anti-allergic use is from about 0.01 mg to about 20 mg (preferably from about 0.1 mg to about 10 mg) of a compound of Formula I per kg of body weight per day and for cytoprotective use from about 0.002 mg to about 100 mg (preferably from about 0.02 mg to about 30 mg and more preferably from about 0.1 mg to about 10 mg) of a compound of Formula I per kg of body weight per day. In the case where an oral composition is employed, a suitable dosage range for anti-asthmatic, or anti-allergic use is, e.g. from about 1 to about 100 mg of a compound of Formula I per kg of body weight per day, preferably from about 5 mg to about 40 mg per kg and for cyto-protective use from about 0.01 mg to about 100 mg (preferably from about 0.1 mg to about 30 mg and were preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser, or a powder which may be formulated as a cartridge from which the powder composition may be inhaled with the aid of a suitable device. The preferred delivery system for inhalation is a metered dose inhalation (MDI) aerosol, which may be formulated as a suspension or solution in fluorocarbon propellants.

Suitable topical formulations of compound I include transdermal devices, aerosols, creams, ointments, lotions, dusting powder, and the like.

In practical use, a compound of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
| --- | --- |
| Compound of Formula I | 2.0 |
| Methylcellulose | 5.0 |

-continued

| Tablet | mg/tablet |
| --- | --- |
| Tween 80 | 0.5 |
| Benzyl alcohol | 9.0 |
| Benzalkonium chloride | 1.0 |
| Water for injection to a total volume of | 1 ml |

| Tablet | mg/tablet |
| --- | --- |
| Compound of Formula I | 25.0 |
| Microcrystalline Cellulose | 415.0 |
| Providone | 14.0 |
| Pregelatinized Starch | 43.5 |
| Magnesium Stearate | 2.5 |
| | 500 |

| Capsule | mg/capsule |
| --- | --- |
| Compound of Formula I | 25.0 |
| Lactose Powder | 573.5 |
| Magnesium Stearate | 1.5 |
| | 600 |

In addition to the compounds of Formula I, the pharmaceutical compositions of the present invention can also contain other active ingredients, such as non-steroidal anti-inflammatory drugs (NSAIDs), peripheral analgesic agents such as zomepirac, diflunisal and the like, cyclooxygenase inhibitors, leukotriene antagonists, leukotriene biosynthesis inhibitors, H$_2$-receptor antagonists, antihistaminic agents, prostaglandin antagonists, ACE inhibitors, and thromboxane synthetase inhibitors. The weight ratio of the compound of the Formula I to the second active ingredient may be varied and will depend upon the effective dose of each ingredient. Generally, an effective dose of each will be used. Thus, for example, when a compound of the Formula I is combined with a second active ingredient the weight ratio of the compound of the Formula I to the second ingredient will generally range from about 1000:1 to about 1:1000, preferably from 200:1 to 1:200. Combinations of a compound of the Formula I and other active ingredients will generally be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof. NSAIDS which are within the scope of this invention are those disclosed in EP 140,684.

Pharmaceutical compositions comprising the Formula I compounds may also contain other inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984), which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, other prostaglandin antagonists such as those disclosed in European Patent Application 11,067 (May 28, 1980) or other thromboxane antagonists such as those disclosed in U.S. Pat. No. 4,237,160. They may also contain histidine decarboxyase inhibitors such as α-fluoromethyl-histidine, described in U.S. Pat. No. 4,325,961. The compounds of the Formula I may also be advantageously combined with an H$_1$ or H$_2$-receptor antagonist, such as for instance benadryl, dramamine, histadyl, phenergan, terfenadine, acetamazole, cimetidine, ranitidine, famotidine, aminothiadiazoles disclosed in EP 40,696 (Dec. 2, 1981) and like compounds, such as those disclosed in U.S. Pat. Nos. 4,283,408; 4,362,736; 4,394,508; and a pending application, U.S. Ser. No. 301,616, filed Sept. 14, 1981. The pharmaceutical compositions may also contain a K$^+$/H$^+$ ATPase inhibitor such as omeprazole, disclosed in U.S. Pat. No. 4,255,431, and the like. Compounds of I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, Vol. 316, pages 126–131, 1985, and the like. Each of the references referred to in this paragraph is hereby incorporated herein by reference.

When the second active ingredient in compositions of this invention is a thromboxane synthetase inhibitor, such inhibitor can be as described in UK 2,038,821 (e.g., UK 37248 and dazoxiben hydrochloride), U.S. Pat No. 4,217,357 (e.g., UK 34787), U.S. Pat. No. 4,444,775 (e.g., CGS 13080), U.S. Pat. No. 4,226,878 (e.g., ONO 046), U.S. Pat. No. 4,495,357 (e.g., U63557A) U.S. Pat. No. 4,273,782 (e.g., UK-38485), or EP 98,690 (e.g., CV-4151).

An embodiment of the invention is a cardiovascular composition useful for treating arterial thrombosis which comprises an antithrombotic compound of the Formula I.

A further embodiment of the invention is a cardiovascular composition useful for treating arterial thrombosis which comprises: (1) the antithrombotic Formula I compound defined above; and, (ii) an angiotensin converting enzyme (ACE) inhibitor compound which is a member of the group: carboxyalkyl dipeptide derivatives; captopril [1-(3-mercapto-2-methyl-1-oxopropyl)-L-proline]; 2-[N-(S)-1-ethoxycarbonyl-3-phenylpropyl)-S-alanyl]-cis,endo-2-azabicyclo[3,3,0]octane-3(S)-carboxylic acid; N-((S)-1-ethoxycarbonyl-3-phenylpropyl)-L-alanyl-N-(2-indanyl)glycine; 1-(N-[(S)-1-ethoxy-carbonyl-3-phenylpropyl]-L-alanyl)-cis,-syn-octahydro-(H-indole-2-S)-carboxylic acid; 2-(N-[(S)-1-ethoxy-carbonyl-3-phenylpropyl]-L-alanyl)-1,2,3,4-tetrahydro-iso-isoquinoline-3(S)-carboxylic acid; and, 1-carboxy-methyl-3(S)-(1(S)-ethoxycarbonyl-3-phenylpropylamino)-2,3,4,5-tetrahydro-1H[1]-benzazepine-2-one.

In particular the class of ACE inhibitors which have been found to have a potentiating effect when used in combination with the Formula I compounds are those disclosed in U.S. Pat. 4,374,829, which also discloses methods for their preparation and which patent is incorporated herein by reference. Of the carboxyalkyl dipeptides disclosed in U.S. Pat. No. 4,374,829, those of particular interest in this invention are N-[1(S)-ethoxycarbonyl-3-phenylpropyl]-L-alanyl-L-proline, also known and referred to herein as enalapril; N-[1(S)-carboxy-3- phenylpropyl]-L-alanyl-L-proline, also know and referred to herein as enalapril diacid; and, Nα-[1(S)-carboxy-3-phenylpropyl]-L-lysyl-L-proline, also known and referred to herein as lisinapril.

The combination composition of the invention can contain varying amounts of (i) the Formula I antithrombotic compound and (ii) ACE inhibitor antihypertensive compounds. The weight ratio of (i):(ii) can range from about 25 to 1; preferably from about 10 to 1. In addition to the active ingredients of (i) alone or of (i) and (ii) in combination, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the present composition.

The combination compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration. These compositions are formulated similarly to the compositions discussed above.

Treatment dosage for human beings for cardiovascular use can be varied as necessary. Generally, daily dosages of the composition of the invention can range from about 6000 to about 10 mg; preferably, from about 3000 to about 20 mg.

The amount of active ingredient that may be combined with the carrier materials to produce a single dosage form for cardiovascular use will vary depending upon the host treated and the particular mode of administration. For example, a formulation intended for oral administration may contain from 5 mg to 5 gm of active agents compounded with an appropriate and convenient amount of carrier material which may vary from about 5 to about 95 percent of the total composition. Dosage unit forms will generally contain between from about 20 mg to about 500 mg of active ingredients.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing thereapy.

The composition of this invention inhibits platelet accumulation at the damaged endothelial surface via the Formula I compound. This inhibitory effect is potentiated by the presence of the antihypertensive compound.

Thus, the compositions of the invention are useful in treating thrombosis and are also of value in the management of acute and chronic congestive heart failure, and limitation of myocardial infarct damage.

In vivo testing of the composition of this invention in test animals (rabbits) can be used to demonstrate that this composition is pharmaceutically effective in decreasing platelet-related arterial thrombic formation.

To demonstrate the potentiation of the antihypertensive compound on the anti-thrombotic Formula I compound comprising the combination composition of the invention, the effect of these compounds on test animals (rabbits) can be determined separately and then in combination. The effect of a different class of antihypertensive agents singly and in combination with the Formula I compound of the invention can also be determined for comparative purposes. The methods employed are described in U.S. Pat. No. 4,558,037 which is hereby incorporated by reference.

The following examples illustrate the preparation of the compounds of the present invention without, however, limiting the same thereto.

All temperature are in degrees Celsius.

EXAMPLE 1

Ethyl 9-p-chlorobenzyl-6-fluoro-1,2,3,4-tetrahydrocarbazol-1-yl-acetate

To 3.50 g of 1-(4-chlorobenzyl)-1-(4-fluorophenyl)-hydrazine hydrochloride in 70 cc of iso-propan. (was added 2.23 g of ethyl 2-cyclohexanone acetate. The reaction was refluxed under nitrogen for 16 hours. The resulting reaction mixture was then evaporated to dryness and the residue suspended in ether. The solid material was then filtered. The ether filtrate was washed with water, dried and evaporated. The resulting syrup was chromatographed on silica gel to give 2.8 g (42%) of the title compound.

$^1$H NMR δ: 1.25 (t, 3H, $CO_2CH_2\underline{CH_3}$); 1.80–2.00 (m, 4H); 2.35–2.85 (m, 4H); 3.38 (m, 1H); 4.10 (q, 2H, $CO_2\underline{CH_2}CH_3$); 5.28 (2d, 2H, Ar $\underline{CH_2}$); 6.80–7.30 (m, 7H, Ar).

EXAMPLE 2

Methyl 3-(9-p-chlorobenzyl-6-fluoro-1,2,3,4-tetrahydrocarbazol-1-yl)-propanoate

Following the procedure of Example 1, but using 1-(4-chlorobenzyl)-1-(4-fluorophenyl)hydrazine hydrochloride and methyl 2-cyclohexanone propionate as starting materials, the title compound is prepared.

EXAMPLE 3

Methyl 3-(9-p-chlorobenzyl-6-methoxy-1,2,3,4-tetrahydrocarbazol-1-yl)-propanoate Following the procedure of Example 1, but using 1-(4-chlorobenzyl)-1-(4-methoxyphenyl)hydrazine hydrochloride and methyl 2-cyclohexanone propionate as starting materials, the title compound is prepared.

EXAMPLE 4

Ethyl 9-p-chlorobenzyl-6-methoxy-1,2,3,4-tetrahydrocarbazol-1-yl-acetate

Following the procedure of Example 1, but using 1-(4-chlorobenzyl)-1-(4-methoxyphenyl)hydrazine hydrochloride and ethyl 2-cyclohexanone acetate as starting materials, the title compound is prepared.

EXAMPLE 5

Ethyl 9-benzyl-6-fluoro-1,2,3,4-tetrahydrocarbazol-1-yl-acetate

Following the procedure of Example 1, but using 1-(benzyl)-1-(4-fluorophenyl)hydrazine hydrochloride and ethyl 2-cyclohexanone acetate as starting materials, the title compound was prepared.

¹HNMRδ: 1.15 (t, 3H, CO₂CH₂CH₃); 1.80–2.00 (m, 4H); 2.38–2.85 (m, 4H); 3.45 (m, 1H); 4.10 (q, 2H, CO₂CH₂CH₃); 5.30 (2d, 2H, Ar CH₂); 6.78–7.25 (m, 8H, Ar).

EXAMPLE 6

Ethyl 9-p-methoxybenzyl-6-fluoro-1,2,3,4-tetrahydrocarbazol-1-yl-acetate

Following the procedure of Example 1, but using 1-(4-methoxybenzyl)-1-(4-fluorophenyl)hydrazine hydrochloride and ethyl 2-cyclohexanone acetate as starting materials, the title compound was prepared.

¹H NMRδ: 1.15 (t, 3H, CO₂, CH₂, CH₃); 1.80–1.95 (m, 4H); 2.40–2.85 (m, 4H); 3.63 (m, 1H); 3.75 (s, 3H, OCH₃); 4.13 (q, 2H, CO₂CH₂CH₃); 5.25 (2d, 2H, Ar CH₂); 6.75–7.25 (m, 7H, Ar).

EXAMPLE 7

Ethyl 9-(3,4-dichloro)benzyl-6-fluoro-1,2,3,4-tetrahydrocarbazol-1-yl-acetate

Following the procedure of Example 1, but using 1-(3,4-dichlorobenzyl)-1-(4-fluorophenyl) hydrazine hydrochloride and ethyl 2-cyclohexanone acetate as starting materials, the title compound was prepared.

¹H NMRδ: 1.15 (t, 3H, CO₂CH₂CH₃); 1.80–2.00 (m, 4H); 2.30–2.85 (m, 4H); 3.35 (m, 1H); 4.15 (q, 2H, CO₂CH₂CH₃); 5.25 (2d, 2H, Ar CH₂); 6.70–7.45 (m, 6H, Ar).

EXAMPLE 8

Ethyl 9-[1-(1-phenyl)ethyl]-6-fluoro-1,2,3,4-tetrahydrocarbazol-1-yl-acetate

Following the procedure of Example 1, but using 1-[1-(1-phenyl)ethyl]-1-(4-fluorophenyl)hydrazine hydrochloride and ethyl 2-cyclohexanone acetate as starting materials, the title compound was prepared.

H NMRδ: 1.15 (t, 3H, CO₂CH₂CH₃); 1.80–2.00 (m, 4H); 2.05 (d, 3H, Ar—CH—Me); 2.50–2.85 (m, 4H); 4.55 (m, 1H); 4.20 (Q, 2H, CO₂CH₂CH₃); 5.65 (q, 1H, Ar—CH—CH₃); 6.60–7.40 (m, 8H, Ar).

EXAMPLE 9

Ethyl 9-p-chlorobenzyl-1,2,3,4-tetrahydrocarbazol-1-yl-acetate

Following the procedure of Example 1, but using 1-(4-chlorobenzyl)-1-(phenyl)hydrazine hydrochloride and ethyl 2-cyclohexanone acetate as starting materials, the title compound was prepared.

H NMRδ: 1.25 (t, 3H, CO₂CH₂CH₃); 1.80–2.00 (m, 4H); 2.38–2.88 (m, 4H); 3.40 (m, 1H); 4.15 (q, 2H, CO₂CH₂CH₃); 4.30 (2d, 2H, Ar CH₂); 6.85–7.55 (m, 8H, Ar).

EXAMPLE 10

Ethyl 9-p-chlorobenzyl-6-chloro-1,2,3,4-tetrahydrocarbazol-1-yl-acetate

Following the procedure of Example 1, but using 1-(4-chlorobenzyl)-1-(4-chlorophenyl)hydrazine hydrochloride and ethyl 2-cyclohexanone acetate as stating materials, the title compound was prepared.

H NMRδ: 1.25 (t, 3H, CO₂CH₂CH₃); 1.80–2.00 (m, 4H); 2.35–2.85 (m, 4H); 3.40 (m, 1H); 4.15 (q, 2H, Ar CH₂); 6.82–7.50 (m, 7H, Ar).

EXAMPLE 11

Ethyl 9-p-chlorobenzyl-8-methyl-1,2,3,4-tetrahydrocarbazol-1-yl-acetate

Following the procedure of Example 1, but using 1-(4-chlorobenzyl)-1-(2-methylphenyl)hydrazine hydrochloride and ethyl 2-cyclohexanone acetate as starting materials, the title compound was prepared.

¹H NMR: 1.30 (t, 3H, CO₂CH₂CH₃); 2.00–2.25 (m, 4H); 2.60–3.15 (m, 4H); 3.58 (m, 1H); 4.40 (q, 2H, CO₂CH₂CH₃); 5.78 (2d, 2H, Ar CH₂); 6.95–7.65 (m, 7H, Ar).

EXAMPLE 12

Ethyl 6-bromo-9-p-chlorobenzyl-1,2,3,4-tetrahydrocarbazol-1-yl-acetate

Following the procedure of Example 1, but using 1-(4-chlorobenzyl)-1-(4-bromophenyl)hydrazine hydrochloride and ethyl 2-cyclohexanone acetate as starting materials, the title compound is prepared.

EXAMPLE 13

Ethyl 9-p-chlorobenzyl-6-methyl-1,2,3,4-tetrahydrocarbazol-1-yl-acetate

Following the procedure of Example 1, but using 1-(4-chlorobenzyl)-1-(4-methylphenyl)hydrazine hydrochloride and ethyl 2-cyclohexanone acetate as starting materials, the title compound is prepared.

EXAMPLE 14

Methyl 2-(9-p-chlorobenzyl-6-fluoro-1,2,3,4-tetrahydrocarbazol-1-yl)-propanoate

Following the procedure of Example 1, but using 1-(4-chlorobenzyl)-1-(4-fluorophenyl)hydrazine hydrochloride and methyl 2-(2-cyclohexanone)propionate as starting materials, the title compound was prepared.

¹H NMRδ: 0.98 (d, 3H, CH₃ CH—CO₂ Me); 1.72–2.00 (m, 4H); 2.60–2.85 (m, 3H); 3.35 (m, 1H); 3.64 (s, 3H, CO₂Me); 5.27 (2d, 2H, Ar—CH₂); 6.75–7.25 (m, 7H, Ar).

EXAMPLE 15

Ethyl 9-p-chlorobenzyl-8-fluoro-1,2,3,4-tetrahydrocarbazol-1-yl-acetate

Following the procedure of Example 1, but using 1-(4-chlorobenzyl)-1-(2-fluorophenyl)hydrazine hydrochloride and ethyl 2-cyclohexanone acetate as starting materials, the title compound was prepared.

¹H NMRδ: 1.25 (t, 3H, CO₂ CH₂ CH₃); 1.50–2.00 (m, 4H); 2.38–2.95 (m, 4H); 3.38 (m, 1H); 4.15 (q, 2H, CO₂CH₂CH₃); 5.45 (2d, 2H, Ar CH₂); 6.78–7.40 (m, 7H, Ar).

EXAMPLE 16

Ethyl 9-p-chlorobenzyl-5,7-dichloro-1,2,3,4-tetrahydrocarbazol-1-yl-acetate

Following the procedure of Example 1, but using 1-(4-chlorobenzyl)-1-(3,5-dichlorophenyl)hydrazine hydrochloride and ethyl 2-cyclohexanone acetate as starting materials, the title compound is prepared.

EXAMPLE 17

Ethyl 9-p-chlorobenzyl-6,8-dichloro-1,2,3,4-tetrahydrocarbazol-1-yl-acetate

Following the procedure of Example 1, but using 1-(4-chlorobenzyl)-1-(2,4-dichlorophenyl)hydrazine hydrochloride and ethyl 2-cyclohexanone acetate as starting materials, the title compound is prepared.

EXAMPLE 18

(−)9-p-chlorobenzyl-6-fluoro-1,2,3,4-tetrahydrocarbazol-1-yl-acetic acid, methyl ester Step I To 1.59 g of ethyl ester from Example 1, in 10 cc of methanol was added 10 cc of water and 420 mg of potassium hydroxide. The resulting solution was refluxed for 4 hours. Upon cooling the reaction mixture was then acidified with HCl (1N). The resulting precipitate was filtered and washed with water. Analytically pure material was prepared by triturating the solid with a mixture of hexane/ethyl acetate (9:1) followed by filtration and drying on a high vacuum pump to give 1.24 g of the racemic acid.

| Analysis calculated for $C_{21}H_{19}NClFO_2$ | | | | |
|---|---|---|---|---|
| C | H | N | Cl | F |
| Calculated 67.83 | 5.15 | 3.77 | 9.53 | 5.11 |
| Found 67.88 | 5.47 | 3.63 | 9.52 | 5.12 |

Step II 10.0 g of 9-p-chlorobenzyl-6-fluoro-1,2,3,4-tetrahydrocarbazol-1-yl-acetic acid from Step I was dissolved in a mixture of hot (refluxing) acetonitrile (150 cc) and ethanol (25 cc), and 4.4 g of d(+) ephedrine was added. The reflux was continued for 15 minutes and the hot solution was filtered and allowed to cool to room temperature. Crystals separated from the solution and were separated by filtration. After three recrystallizations form acetonitrile 3.9 g of the pure salt was obtained.

Step III 3.9 g of pure salt from Step II was dissolved in 200 cc of methanol and acidified using 1N hydrochloric acid. Water was added and the crystals were separated by filtration and dryed under vacuum. Upon trituration with hexane-ethyl acetate (9:1) the resolved acid was prepared.

αD = −42.5 (methanol) m.p. 151°–151.5° C.

Step IV

To a solution of 1.0 g of the acid from Step III in 50 ml of ether is added a solution of diazomethane in ether until a slight excess of diazomethane is present. The excess diazomethane is destroyed by addition of a few drops of acetic acid. The reaction mixture is washed with 50 ml of 5% $Na_2CO_3$ solution, water, and dried over $MgSO_4$. Filtration and evaporation of the solvent leaves the title compound.

EXAMPLE 19

(+) 9-p-chlorobenzyl-6-fluoro-1,2,3,4-tetrahydrocarbazol-1-yl-acetic acid, methyl ester Following the method of Example 18, but using 1(−) ephedrine in Step II, there is obtained the title compound.

EXAMPLE 20

Ethyl 9-p-chlorobenzyl-6-isopropyl-1,2,3,4-tetrahydrocarbazol-1-yl-acetate

Following the procedure of Example 1, but using 1-(4-chlorobenzyl)-1-(4-isopropylphenyl) hydrazine hydrochloride and ethyl 2-cyclohexanone acetate as starting materials, the title compound was prepared as a mixture of ethyl and isopropyl esters.

EXAMPLE 21

Ethyl 9-p-chlorobenzyl-6-tert-butyl-1,2,3,4-tetrahydrocarbazol-1-yl-acetate

Following the procedure of Example 1, but using 1-(4-chlorobenzyl)-1-(4-tert-butylphenyl) hydrazine hydrochloride and ethyl 2-cyclohexanone acetate as starting materials, the title compound was prepared as a mixture of ethyl and isopropyl esters.

EXAMPLE 22

Ethyl 9-p-chlorobenzyl-6-trifluoromethyl-1,2,3,4-tetrahydrocarbazol-1-yl-acetate Following the procedure of Example 1, but using 1-(4-chlorobenzyl)-1-(4-trifluoromethylphenyl) hydrazine hydrochloride and ethyl 2-cyclohexanone acetate as starting materials, the title compound was prepared as a mixture of ethyl and isopropyl esters.

EXAMPLE 23

Ethyl 9-p-chlorobenzyl-6-methylthio-1,2,3,4-tetrahydrocarbazol-1-yl-acetate

Following the procedure of Example 1, but using 1-(4-chlorobenzyl)-1-(4-methylthiophenyl) hydrazine hydrochloride and ethyl 2-cyclohexanone acetate as starting materials, the title compound was prepared as a mixture of ethyl and isopropyl esters. The pure title compound was obtained by purification on a flash chromatogram.

EXAMPLE 24

Ethyl 9-p-chlorobenzyl-6-methylsulfinyl-1,2,3,4-tetrahydrocarbazol-1-yl-acetate

To 498 mg of ethyl 9-p-chlorobenzyl-6-methylthio-1,2,3,4-tetrahydrocarbazol-1-yl-acetate from Example 23 in 10 cc of methylene chloride was added 300 mg of m-chloro perbenzoic acid. The resulting mixture was stirred for 1.5 hours at room temperature. The reaction mixture was diluted with ether and consecutively washed with a solution of sodium bicarbonate, water and brine. The crude product obtained after evaporation of the organic layer was purified on silica gel by flash chromatography eluting with 20% hexane/ethyl acetate and yielded 420 mg (82%) of the pure title compound.

EXAMPLE 25

Ethyl 9-p-chlorobenzyl-6-methylsulfonyl-1,2,3,4-tetrahydrocarbazol-1-yl-acetate

To 439 mg of ethyl 9-p-chlorobenzyl-6-methylsulfinyl-1,2,3,4-tetrahydrocarbazol-1-yl-acetate from Example 24, in 10 cc of methylene chloride was added 353 mg of m-chloro perbenzoic acid. The resulting mixture was stirred for 18 hours at room temperature. The reaction mixture was diluted with ether and washed consecutively with a solution of sodium bicarbonate, water and brine. The crude product obtained after evaporation of the organic layer was purified on silica gel by flash chromatography eluting with 30% hexane/ethyl acetate and yielded 200 mg (42%) of the pure title compound.

EXAMPLE 26

Ethyl 9-p-chlorobenzyl-8-isopropyl-1,2,3,4-tetrahydrocarbazol-1-yl-acetate

Following the procedure of Example 1, but using 1-(4-chlorobenzyl)-1-(2-isopropylphenyl) hydrazine hydrochloride and ethyl 2-cyclohexanone acetate as starting materials, the title compound was prepared as a mixture of ethyl and isopropyl esters.

EXAMPLE 27

9-p-Chlorobenzyl-8-methylthio-1,2,3,4-tetrahydrocarbazol-1-yl-acetic acid, methyl ester Following the procedure of Example 30, but using 1-(2-methylthiophenyl) hydrazine hydrochloride and ethyl 2-cyclohexanone acetate as starting materials, the title compound was prepared.

EXAMPLE 28

9-p-Chlorobenzyl-8-methylsulfinyl-1,2,3,4-tetrahydrocarbazol-1-yl-acetic acid, methyl ester Following the procedure of Example 24, but using methyl ester from Example 27, there is obtained the title compound.

EXAMPLE 29

Ethyl 9-p-chlorobenzyl-6-fluoro-3-methyl-1,2,3,4-tetrahydrocarbazol-1-yl-acetate Following the procedure of Example 1, but using 1-(4-chlorobenzyl)-1-(4-fluorophenyl) hydrazine hydrochloride and ethyl 4-methyl-2-cyclohexanone acetate as starting materials, the title compound was prepared as a mixture of ethyl and isopropyl esters.

EXAMPLE 30

9-p-Chlorobenzyl-6,8-difluoro-1,2,3,4-tetrahydrocarbazol-1-yl-acetic acid, methyl ester Step I To 114 g of 1-(2,4-difluorophenyl) hydrazine hydrochloride in 350 cc of 2-propanol containing 40 cc of acetyl chloride was added 138 g of ethyl 2-cyclohexanone acetate. The reaction was refluxed under nitrogen for 2 days. After cooling, 200 cc of ether was added and the precipitate filtered. The filtrate was evaporated to dryness. The resulting residue was dissolved in a (1:1) mixture of ether/ethyl acetate and consecutively ashed with water, sodium bicarbonate solutin and brine. The organic layer was dried over sodium sulfate and evaporated to dryness. The crude product was passed through a silica gel bed eluting with 5% ethyl acetate/hexane to yield 84 g of a 1:2 mixture of ethyl and isopropyl esters.

Step II 84 g of esters from Step I was dissolved in 250 cc of methanol and 400 cc of sodium hydroxide (1N) was added and refluxed 4 hours. After cooling, the reaction mixture was washed with a (1:1) mixture of ether/hexane and the aqueous layer was acidified with HCl (1N). The resulting precipate was filtered, washed with water and air dried to afford 50 g of 6,8-difluoro-1,2,3,4-tetrahydrocarbazol-1-yl-acetic acid.

Step III

A solution of 11.1 g of acid from Step II in 100 cc of THF was added portionwise 10.3 g of potassium tert-butoxide. The resulting mixture was stirred for 45 min at room temperature and 10.3 g p-chlorobenzyl bromide was added portionwise. The reaction mixture was stirred 18 hours at room temperature. The resulting mixture was diluted with 100 cc of water and washed with hexane. The aqueous layer was acidified with HCl (1N) and the resulting precipitate filtered, washed with water and air-dried to afford 9.4 g of 9-p-chlorobenzyl-6,8-difluoro-1,2,3,4-tetrahydrocarbazol-1-yl-acetic acid.

Step IV

Following the method of Example 18, Step IV but using the acid of Step III, there was obtained the title compound.

$^1$H NMR (CDCl$_3$) δ 1.75–2.00 (m, 4H, (CH$_2$)$_2$) 2.38–2.78 (m, 4H, $\underline{\text{CH}_2}$CO$_2$Me, $\underline{\text{CH}_2}$—C=C), 3.35–3.45 (m, 1H, CH—C=$\overline{\text{C}}$), 3.70 (s, 3H, CO$_2$Me), 5.40 (dd, 1H, $\underline{\text{CH}_2}$—Ar), 6.60 (ddd, 1H, H$_7$), 6.92 (dd, 1H, H$_5$), 6.82 and 7.22 (2d, 4H, Ar).

EXAMPLE 31

9-p-Chlorobenzyl-6,8-dimethyl-1,2,3,4-tetrahydrocarbazol-1-yl-acetic acid, methyl ester Following the procedure of Example 30, but using 1-(2,4-dimethylphenyl) hydrazine hydrochloride and ethyl 2-cyclohexanone acetate in Step I, as starting materisl, the title compound is prepared.

EXAMPLE 32

9-p-Chlorobenzyl-6-methoxy-8-methyl-1,2,3,4-tetrahydrocarbazol-1-yl-acetic acid, methyl ester Following the procedure of Example 30, but using 1-(4-methoxy-2-methylphenyl) hydrazine hydrochloride and ethyl 2-cyclohexanone acetate in Step I, as starting material, the title compound is prepared.

EXAMPLE 33

(−) 9-p-Chlorobenzyl-6,8-difluoro-1,2,3,4-tetrahydrocarbazol-1-yl-acetic acid, methyl ester Following the method of Example 18, Step II to Step IV, but using 9-p-chlorobenzyl-6,8-difluoro-1,2,3,4-tetrahydrocarbazol-1-yl-acetic acid from Example 30, Step III and using d(+)ephedrine in Step III, there was obtained the title compound.

$^1$H NMR (CDCl$_3$) δ 1.75–2.00 (m, 4H, (CH$_2$)$_2$) 2.38–2.78 (m, 4H, C$\underline{H}_2$CO$_2$Me, CH$_2$—C≡C), 3.35–3.45 (m, 1H, CH—C≡C), 3.70 (s, 3H, CO$_2$Me), 5.40 (dd, 1H, CH$_2$Ar), 6.60 (ddd, 1H, 4$_7$), 6.92 (dd, 1H, H$_5$), 6.82 and 7.22 (2d, 4H, Ar).

EXAMPLE 34

(+) 9-p-Chlorobenzyl-6,8-difluoro-1,2,3,4-tetrahydrocarbazol-1-yl-acetic acid, methyl ester Following the method of Example 18, Step II to Step IV, but using 9-p-chlorobenzyl-6,8-difluoro-1,2,3,4-tetrahydrocarbazol-1-yl-acetic acid from Example 30, Step III and using l(−)ephedrine in Step III, there is obtained the title compound.

EXAMPLE 35

(−) 9-p-Chlorobenzyl-8-methyl-1,2,3,4-tetrahydrocarbazol-1-yl-acetic acid, methyl ester Following the method of Example 18, but using the ethyl ester from Example 11 in Step I and using d(+)ephedrine in Step II, there is obtained the title compound.

EXAMPLE 36

(+) 9-p-Chlorobenzyl-8-methyl-1,2,3,4-tetrahydrocarbazol-1-yl-acetic acid, methyl ester Following the method of Example 18, but using ethyl ester from Example 11 in Step I and using l(−)ephedrine in Step II, there is obtained the title compound.

EXAMPLE 37

(−) 9-p-Chlorobenzyl-8-fluoro-1,2,3,4-tetrahydrocarbazol-1-yl-acetic acid, methyl ester Following the method of Example 18, but using the ethyl ester from Example 15 in Step I and using d(+)ephedrine in Step II, there is obtained the title compound.

EXAMPLE 38

(+) 9-p-Chlorobenzyl-8-fluoro-1,2,3,4-tetrahydrocarbazol-1-yl-acetic acid, methyl ester Following the method of Example 18, but using the ethyl ester from Example 15 in Step I and using l(−)ephedrine in Step II, there is obtained the title compound.

EXAMPLE 39

9-o-Chlorobenzyl-6,8-difluoro-1,2,3,4-tetrahydrocarbazol-1-yl-acetic acid, methyl ester Step I A solution of 200 mg of 6,8-difluoro-1,2,3,4-tetrahydrocarbazol-1-yl-acetic acid from Example 30 Step II in 8 cc of DMF was added portionwise 40 mg of sodium hydride. The resulting mixture was stirred for 30 min. at room temperature and 185 mg of o-chlorobenzyl bromide was then added. After stirring overnight at room temperature, the resulting mixture was diluted with water and washed with ether. The aqueous layer was acidified with (1N) HCl and extracted with ether. The ethereal layer was washed with brine, dried over Na$_2$SO$_4$ and evaporated to dryness. The crude product was purified on preparative plates (silica gel) eluting with CHCl$_3$:MeOH:NH$_4$OH (8:4:1) to yield 98 mg of 9-o-chlorobenzyl-6,8-difluoro-1,2,3,4-tetrahydrocarbazol-1-yl-acetic acid, m.p. 197°–198° C.

Step II

Following the method of Example 18, Step IV but using the acid of Step I, there is obtained the title compound.

EXAMPLE 40

9-(2,4-Dichlorobenzyl)-6,8-difluoro-1,2,3,4-tetrahydrocarbazol-1-yl-acetic acid, methyl ester Following the procedure of Example 39, but substituting 2,4-dichlorobenzyl chloride for o-chloro benzyl bromide as starting material, the title compound is obtained.

EXAMPLE 41

9-p-Methylthiobenzyl-6,8-difluoro-1,2,3,4-tetrahydrocarbazol-1-yl-acetic acid, methyl ester Following the procedure of Example 39, but substituting p-methylthiobenzyl chloride for o-chlorobenzyl bromide as starting material, the title compound is obtained.

EXAMPLE 42

9-p-Methylsulfinylbenzyl-6,8-difluoro-1,2,3,4-tetrahydrocarbazol-1-yl-acetic acid, methyl ester Following the procedure of Example 39, but substituting p-methylsulfinylbenzyl chloride for o-chlorobenzyl bromide as starting material, the title compound is obtained.

EXAMPLE 43

9-p-Methylsulfonylbenzyl-6,8-difluoro-1,2,3,4-tetrahydrocarbazol-1-yl-acetic acid, methyl ester Step I To a cold solution (0° C.) of 4.0 g of 6,8-difluoro-1,2,3,4-tetrahydrocarbazol-1-yl-acetic acid, from Example 30, Step II, in 75 cc of tetrahydrofuran was added dropwise 46.3 cc of a solution of potassium hexamethyldisilazide (KHMDS) in toluene (0.684M) and stirred for 10 minutes. To the resulting cold (0° C.) solution was added dropwise 3.7 g of a solution of p-methylsulfonylbenzyl chloride in 12 cc of tetrahydrofuran. The reaction mixture was then stirred at room temperature for 2 hours. The reaction mixture was diluted with water and washed with ether. The aqueous layer was acidified with (1N) HCl and extracted with ethyl acetate. The organic layer was washed with brine, dried over Na$_2$SO$_4$ and evaporated to dryness. The residue was triturated with a mixture of ethylacetate:hexane (3:7) and filtered to yield 5.1 g of 9-p-methylsulfonylbenzyl-6,8-difluoro-1,2,3,4-tetrahydrocarbazol-1-yl-acetic acid, m.p. 217°–219° C.

Step II

Following the method of Example 18, Step IV but using the acid of Step I, there was obtained the title compound, m.p. 169°–170° C.

EXAMPLE 44

(−)9-p-Methylsulfonylbenzyl-6,8-difluoro-1,2,3,4-tetrahydrocarbazol-1-yl-acetic acid, methyl ester Following the method of Example 18, Step II to Step IV, but using 9-p-methylsulfonylbenzyl-6,8-difluoro- 1,2,3,4-tetrahydrocarbazol-1-yl-acetic acid from Example 43, Step I and using l(−) ephedrine, there was obtained the title compound, m.p. 116°–117° C.

EXAMPLE 45

(+)9-p-Methylsulfonylbenzyl-6,8-difluoro-1,2,3,4-tetrahydrocarbazol-1-yl-acetic acid, methyl ester Following the method of Example 18, Step II to Step IV, but using 9-p-methsulfonylbenzyl-6,8-difluoro-1,2,3,4-tetrahydrocarbazol-1-yl-acetic acid from Example 43, Step I and using d(+) ephedrine, there is obtained the title compound.

EXAMPLE 46

9-p-Trifluoromethylbenzyl-6,8-difluoro-1,2,3,4-tetrahydrocarbazol-1-yl-acetic acid, methyl ester Following the procedure of Example 39, but substituting p-trifluoromethylbenzyl bromide for o-chlorobenzyl bromide as starting material, the title compound is obtained.

EXAMPLE 47

9-p-Fluorobenzyl-6,8-difluoro-1,2,3,4-tetrahydrocarbazol-1-yl-acetic acid, methyl ester Following the procedure of Example 39, but substituting p-fluorobenzyl bromide for o-chlorobenzyl bromide as starting material, the title compound is obtained.

EXAMPLE 48

9-m-Chlorobenzyl-6,8-difluoro-1,2,3,4-tetrahydrocarbazol-1-yl-acetic acid, methyl ester Following the procedure of Example 39, but substituting m-chlorobenzyl bromide for o-chlorobenzyl bromide as starting material, the title compound is obtained.

EXAMPLE 49

9-p-Carbomethoxybenzyl-6,8-difluoro-1,2,3,4-tetrahydrocarbazol-1-yl-acetic acid, methyl ester Following the procedure of Example 39, but substituting p-carbomethoxybenzyl chloride for o-chlorobenzyl bromide as starting material, the title compound is obtained.

EXAMPLE 50

9-p-Dimethylcarboxamidobenzyl-6,8-difluoro-1,2,3,4-tetrahydrocarbazol-1-yl-acetic acid, methyl ester Following the procedure of Example 39, but substituting p-dimethylcarboxamidobenzyl chloride for o-chlorobenzyl bromide as starting material, the title compound is obtained.

EXAMPLE 51

9-p-Acetylbenzyl-6,8-difluoro-1,2,3,4-tetrahydrocarbazol-1-yl-acetic acid, methyl ester Following the procedure of Example 39, but substituting p-acetylbenzyl chloride for o-chlorobenzyl bromide as starting material, the title compound is obtained.

EXAMPLE 52

9-p-Dimethylaminosulfonylbenzyl-6,8-difluoro-1,2,3,4-tetrahydrocarbazol-1-yl-acetic acid, methyl ester Following the procedure of Example 39, but substituting p-dimethylaminosulfonylbenzyl chloride for o-chlorobenzyl bromide as starting material, the title compound is obtained.

EXAMPLE 53

9-p-Acetamidobenzyl-6,8-difluoro-1,2,3,4-tetrahydrocarbazol-1-yl-acetic acid, methyl ester Step I Following the procedure of Example 39, but substituting p-nitrobenzyl bromide for o-chlorobenzyl chloride as starting material, the crude 9-p-nitrobenzyl-6,8-difluoro-1,2,3,4-tetrahydrocarbazol-1-yl-acetic acid was obtained.

Step II

The crude acid from step I was dissolved in ether and esterified with diazomethane. The reaction was monitored by TLC. The resulting solution was evaporated to dryness and the oily residue was chromatographed on a flash silica gel column eluting with ethyl acetate:hexane mixture (1:4) to afford 4.1 g (from 4.1 g of 6,8-difluoro-1,2,3,4-tetrahydrocarbazol-1-yl-acetic acid used in step I) of pure methyl 9-p-nitrobenzyl-6,8-difluoro-1,2,3,4-tetrahydrocarbazol-1-yl-acetate.

Step III

To a solution of 4.0 g of ester from step II in 40 cc of ethyl acetate and 70 cc of ethanol was added 400 mg of Pd/C (10%) and the resulting mixture was hydrogenated on a Parr hydrogenator for 90 minutes under 30 psi of hydrogen. The reaction mixture was filtered on Celite and the filtrate was evaporated to dryness leaving 3.5 g of the aminoester derivative as a foam.

Step IV

To a solution of 595 mg of the aminoester derivative from step III and 0.325 cc of triethylamine in 10 cc of tetrahydrofuran was added dropwise 0.132 cc of acetyl chloride and the resulting mixture was stirred for 30 minutes at room temperature. The reaction mixture was diluted with water and ether. The ether layer was decanted, washed with brine, dried over $Na_2SO_4$ and evaporated to dryness. The residue was triturated with a mixture of ethylacetate:hexane (3:7) and filtered to afford 600 mg of the title compound.

EXAMPLE 54

9-p-Methylsulfonamidobenzyl-6,8-difluoro-1,2,3,4-tetrahydrocarbazol-1-yl-acetic acid, methyl ester Following the procedure of Example 53, Step IV, but substituting methanesulfonyl chloride for acetyl chloride as starting material, the title product was obtained.

EXAMPLE 55

9-p-Methylureidobenzyl-6,8-difluoro-1,2,3,4-tetrahydrocarbazol-1-yl-acetic acid, methyl ester To a solution of 538 mg of the aminoester derivative from Example 53, Step III in 10 cc of tetrahydrofuran was added 0.3 cc of methylisocyanate and the resulting solution was stirred overnight. The reaction mixture was diluted with water and ether. The ether layer was decanted, washed with brine, dried over $Na_2SO_4$ and evaporated to dryness leaving the title compound.

EXAMPLE 56

9-p-Methoxybenzyl-6,8-difluoro-1,2,3,4-tetrahydrocarbazol-1-yl-acetic acid, methyl ester Following the procedure of Example 39, but substituting p-methoxybenzyl chloride for o-chlorobenzyl bromide as starting material, the title compound is obtained.

What is claimed is:

1. A compound of the formula:

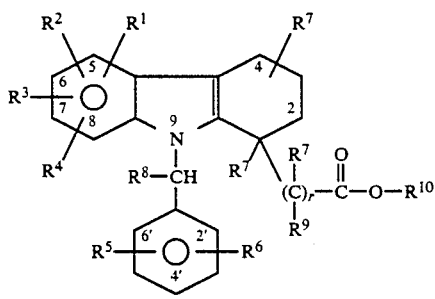

wherein:
$R^1$, $R^2$, $R^3$, $R^4$, $R^5$ and $R^6$ are each independently selected from:
 (1) hydrogen;
 (2) alkyl having 1 to 6 carbons;
 (3) alkenyl having 2 to 6 carbons;
 (4) —(CH$_2$)$_n$M wherein M is
  (a) OR$^{11}$;
  (b) halogen;
  (c) CF$_3$;
  (d) SR$^{11}$;
  (e) phenyl or substituted phenyl;
  (f) COOR$^{12}$;

(g) 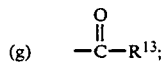

(h) tetrazole;

(i) 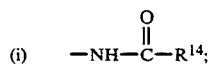

(j) —NR$^{12}$R$^{12}$;
 (k) —NHSO$_2$R$^{15}$;

(l) 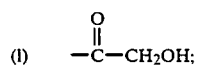

(m) —SOR$^{11}$;
 (n) —CONR$^{12}$R$^{12}$;
 (o) —SO$_2$NR$^{12}$R$^{12}$;
 (p) —SO$_2$R$^{11}$;
 (q) NO$_2$;

(r) 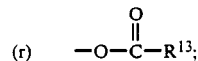

(s) 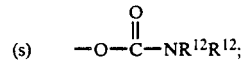

(t) 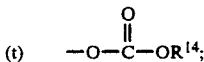

(u) CN; or
 (v) N$_3$;

provided that when $R^1$, $R^2$, $R^3$ or $R^4$ is alkyl having 1 to 6 carbons, it is not located at position 6; provided that at least one of $R^5$ or $R^6$ is M wherein M is
 (d) SR$^{11}$;
 (m) —SOR$^{11}$;
 (o) —SO$_2$NR$^{12}$R$^{12}$; or
 (p) —SO$_2$R$^{11}$;
$R^7$ is H or alkyl of 1 to 6 carbons;
$R^8$ is H or alkyl of 1 to 6 carbons;
each $R^9$ is independently H, OH, C$_1$ to C$_4$-O-alkyl, or alkyl of 1 to 4 carbons;
$R^{10}$ is lower alkyl, substituted or unsubstituted 2-phenethyl, substituted or unsubstituted benzyl, or substituted or unsubstituted phenyl;
each $R^{11}$ is independently H, C$_1$ to C$_6$ alkyl, benzyl, phenyl, or substituted phenyl;
each $R^{12}$ is independently H, phenyl, benzyl, or C$_1$ to C$_6$ alkyl;
each $R^{13}$ is independently H, (CH$_2$)$_m$COOR$^{12}$, C$_1$ to C$_6$ alkyl, CF$_3$, phenyl, or substituted phenyl;
each $R^{14}$ is independently C$_1$ to C$_6$ alkyl, benzyl, or phenyl;
each $R^{15}$ is independently C$_1$ to C$_6$ alkyl, 4-methylphenyl, phenyl, or CF$_3$;
m is 0 to 4;
n is 0 to 3; and
r is 1 to 6;
or a pharmaceutically acceptable salt thereof.

2. A compound according to claim 1, wherein n is 0 or 1.

3. A compound according to claim 2, wherein:
n is 0; and
r is 1 or 2.

4. A compound according to claim 3, wherein:
$R^1$, $R^2$, $R^3$, $R^4$, and $R^5$ are each independently selected from:
 (1) hydrogen;
 (2) alkyl having 1 to 6 carbons;
 (3) M, wherein M is
  (a) OR$^{11}$;
  (b) halogen;
  (c) CF$_3$;
  (d) SR$^{11}$;
  (e) COOR$^{12}$;

(f) 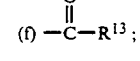

(g) tetrazole;
 (h) —SOR$^{11}$;
 (i) —CONR$^{12}$R$^{12}$;
 (j) —SO$_2$NR$^{12}$R$^{12}$;
 (k) —SO$_2$R$^{11}$;

(l) 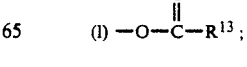

(m) CN; or
 (n) N$_3$;

$R^6$ is located at position 3' or 4' and is selected from:

(1) alkyl having 1 to 6 carbons;

(2) M wherein M is (a) $OR^{11}$;

(b) halogen;

(c) $CF_3$;

(d) $SR^{11}$;

(e) $COOR^{12}$;

(f) 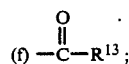

(g) tetrazole;

(h) —$SOR^{11}$;

(i) —$CONR^{12}R^{12}$;

(j) —$SO_2NR^{12}R^{12}$;

(k) —$SO_2R^{11}$;

(l) 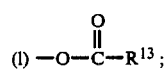

(m) CN; or (n) $N_3$;

each $R^9$ is independently H or alkyl of 1 to 4 carbons;

$R^{10}$ is lower alkyl; and r is 1.

5. A compound according to claim 1 which is:

9-p-Methylthiobenzyl-6,8-difluoro-1,2,3,4-tetrahydrocarbazol-1-yl-acetic acid, methyl ester;

9-p-Methylsulfinylbenzyl-6,8-difluoro-1,2,3,4-tetrahydrocarbazol-1-yl-acetic acid, methyl ester;

9-p-Methylsulfonylbenzyl-6,8-difluoro-1,2,3,4-tetrahydrocarbazol-1-yl-acetic acid, methyl ester;

(—)9-p-Methylsulfonylbenzyl-6,8-difluoro-1,2,3,4-tetrahydrocarbazol-1-yl-acetic acid, methyl ester;

(+)9-p-Methylsulfonylbenzyl-6,8-difluoro-1,2,3,4-tetrahydrocarbazol-1-yl-acetic acid, methyl ester; or 9-p-Dimethylaminosulfonylbenzyl-6,8-difluoro-1,2,3,4-tetrahydrocarbazol-1-yl-acetic acid, methyl ester.

6. A compound according to claim 1, which is a pure optical isomer.

7. A compound according to claim 6, which is the (+)-isomer.

8. A compound according to claim 6, which is the (—)-isomer.

9. A compound of the formula:

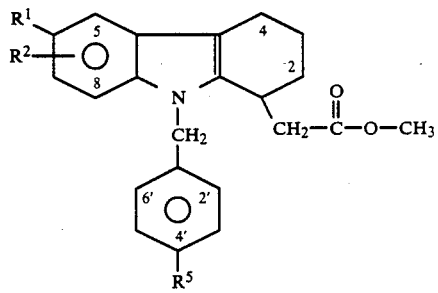

wherein:

| Compound | $R^1$ | $R^2$ | $R^5$ |
|---|---|---|---|
| 46 | F | 8-F | —SMe |
| 47 | F | H | —S(O)Me |
| 49 | F | H | —S(O)$_2$Me |
| 60 (ex. 42) | F | 8-F | —S(O)Me |
| 61 (ex. 43) | F | 8-F | —S(O)$_2$Me |
| 62 (ex. 44) | F (—) isomer | 8-F | —S(O)$_2$Me |
| 63 (ex. 45) | F (+) isomer | 8-F | —S(O)$_2$Me |
| 71 (ex. 52) | F | 8-F | —SO$_2$NMe$_2$ |

10. A pharmaceutical composition for inhibiting leukotriene synthesis and antagonizing prostaglandins in mammals comprising an effective amount of a compound of claim 1 or a pharmaceutically acceptable salt thereof, and a pharmaceutically acceptable carrier.

11. A pharmaceutical composition according to claim 10, wherein n is 0 or 1.

12. A pharmaceutical composition according to claim 11 wherein:

n is 0; and r is 1 or 2.

13. A pharmaceutical composition according to claim 12, wherein:

$R^1$, $R^2$, $R^3$, $R^4$, $R^5$ and $R^6$ are each independently selected from:

(1) hydrogen;

(2) alkyl having 1 to 6 carbons;

(3) M wherein M is (a) $OR^{11}$;

(b) halogen;

(c) $CF_3$;

(d) $SR^{11}$;

(e) $COOR^{12}$;

(f) 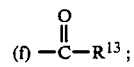

(g) tetrazole;

(h) —$SOR^{11}$;

(i) —$CONR^{12}R^{12}$;

(j) —$SO_2NR^{12}R^{12}$;

(k) —$SO_2R^{11}$;

(l) 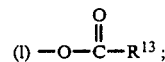

(m) CN; or (n) $N_3$;

$R^{10}$ is lower alkyl; and r is 1.

14. A method of inhibiting leukotriene synthesis in a mammal, which comprises administering to a mammal an effective amount of a compound of claim 1.

* * * * *